US012667414B2

(12) United States Patent　　　(10) Patent No.:　US 12,667,414 B2
Matsuo et al.　　　　　　　　　　(45) Date of Patent:　　　Jun. 30, 2026

(54) ENDOSCOPIC TREATMENT DEVICE AND ENDOSCOPIC TREATMENT METHOD

(71) Applicant: OLYMPUS CORPORATION, Hachioji (JP)

(72) Inventors: Nobuko Matsuo, Hachioji (JP); Keiichi Sato, Hachioji (JP); Takuya Okumura, Hamburg (DE); Yuta Hayashi, Kawasaki (JP)

(73) Assignee: OLYMPUS CORPORATION, Tokyo (JP)

( * ) Notice: Subject to any disclaimer, the term of this patent is extended or adjusted under 35 U.S.C. 154(b) by 990 days.

(21) Appl. No.: 17/858,223

(22) Filed: Jul. 6, 2022

(65) Prior Publication Data

US 2022/0338716 A1　　Oct. 27, 2022

Related U.S. Application Data

(63) Continuation of application No. PCT/JP2020/000451, filed on Jan. 9, 2020.

(51) Int. Cl.
A61B 1/00　　　(2006.01)
A61B 1/005　　　(2006.01)
(Continued)

(52) U.S. Cl.
CPC ........ A61B 18/1492 (2013.01); A61B 1/0008 (2013.01); A61B 1/005 (2013.01);
(Continued)

(58) Field of Classification Search
CPC . A61B 18/042; A61B 18/14; A61B 2018/122; A61B 2018/00589;
(Continued)

(56) References Cited

U.S. PATENT DOCUMENTS 4,562,838 A * 1/1986 Walker ............... A61B 18/1402
　　　　　　　　　　　　　　　　　　606/49
5,318,565 A * 6/1994 Kuriloff ............. A61B 18/1402
　　　　　　　　　　　　　　　　　　606/49
(Continued)

FOREIGN PATENT DOCUMENTS

DE　　102010061059 A1　　4/2012
JP　　H01-015362 Y2　　5/1989
(Continued)

OTHER PUBLICATIONS

Jun. 6, 2023 Office Action issued in Japanese Patent Application No. 2021-570008.
(Continued)

*Primary Examiner* — Darwin P Erezo
*Assistant Examiner* — Mitchell Brian Hoag
(74) *Attorney, Agent, or Firm* — Oliff PLC

(57)　　　　　ABSTRACT

A treatment device and an endoscopic treatment method are disclosed. The treatment device includes a first pipeline that is made of material having electrical insulation, and includes an internal space; an electrode that is energizable with high frequency current; a distal-end tip that is attached to a distal end of the first pipeline, and includes a distal-end opening in communication with the internal space of the first pipeline; and a second pipeline that is inserted through the first pipeline and through which liquid can pass. The endoscopic treatment method includes puncturing a treatment target and performing a local injection using the treatment device.

14 Claims, 26 Drawing Sheets

(51) Int. Cl.

| | |
|---|---|
| *A61B 1/015* | (2006.01) |
| *A61B 1/273* | (2006.01) |
| *A61B 18/14* | (2006.01) |
| *A61B 18/00* | (2006.01) |

(52) U.S. Cl.
CPC ............ *A61B 1/015* (2013.01); *A61B 1/2736* (2013.01); *A61B 2018/00494* (2013.01); *A61B 2018/00595* (2013.01)

(58) Field of Classification Search
CPC ...... A61B 2018/1467; A61B 2018/144; A61B 2018/00595; A61B 2018/00494; A61B 1/2736; A61B 1/015; A61B 1/005; A61B 1/0008; A61B 18/1492
See application file for complete search history.

(56) References Cited

U.S. PATENT DOCUMENTS

| | | | | |
|---|---|---|---|---|
| 5,413,575 | A * | 5/1995 | Haenggi | A61B 18/1402 606/45 |
| 5,626,577 | A * | 5/1997 | Harris | A61B 18/1402 606/49 |
| 5,891,140 | A * | 4/1999 | Ginn | A61B 18/1445 606/45 |
| 6,197,026 | B1 | 3/2001 | Farin et al. | |
| 6,293,945 | B1 * | 9/2001 | Parins | A61B 18/1402 606/49 |
| 7,623,899 | B2 | 11/2009 | Worley et al. | |
| 8,425,509 | B2 * | 4/2013 | Longo | A61B 18/1402 606/45 |
| 9,119,622 | B2 | 9/2015 | Rahmani | |
| 9,289,261 | B2 * | 3/2016 | Shvetsov | A61B 18/1402 |
| 9,592,070 | B2 | 3/2017 | Inoue | |
| 9,795,505 | B2 * | 10/2017 | Yu | A61F 9/00736 |
| 10,675,084 | B2 * | 6/2020 | Lowry | A61B 18/1402 |
| 12,114,910 | B2 * | 10/2024 | Kim | A61M 1/7411 |
| 2007/0066985 | A1 | 3/2007 | Geitz et al. | |
| 2007/0135803 | A1 * | 6/2007 | Belson | A61B 1/00154 606/1 |
| 2007/0213704 | A1 | 9/2007 | Truckai et al. | |
| 2013/0090643 | A1 * | 4/2013 | Williams | A61B 18/042 606/49 |
| 2013/0090644 | A1 * | 4/2013 | Williams | A61B 18/042 606/49 |
| 2014/0005660 | A1 | 1/2014 | Edwards et al. | |
| 2014/0148732 | A1 * | 5/2014 | Radl | A61F 5/0089 600/593 |
| 2015/0005760 | A1 * | 1/2015 | Poulsen | A61B 18/1206 606/34 |
| 2015/0238219 | A1 | 8/2015 | Karwei | |
| 2016/0192979 | A1 * | 7/2016 | Mikkaichi | A61B 90/39 606/49 |
| 2017/0042522 | A1 * | 2/2017 | Kogiso | A61B 1/00087 |
| 2017/0071653 | A1 | 3/2017 | Enderle et al. | |
| 2017/0312029 | A1 | 11/2017 | Schaer | |
| 2019/0069944 | A1 | 3/2019 | Fischer | |
| 2019/0090975 | A1 * | 3/2019 | Hernandez | A61B 18/1402 |
| 2019/0201047 | A1 * | 7/2019 | Yates | A61B 18/1445 |
| 2019/0269429 | A1 * | 9/2019 | Clark, III | A61M 37/00 |
| 2019/0307506 | A1 * | 10/2019 | Gelbart | A61B 90/37 |

FOREIGN PATENT DOCUMENTS

| | | | |
|---|---|---|---|
| JP | H08-336542 A | | 12/1996 |
| JP | 2001178740 A | * | 7/2001 |
| JP | 2002-503508 A | | 2/2002 |
| JP | 2002301088 A | * | 10/2002 |
| JP | 2003-534037 A | | 11/2003 |
| JP | 2007-313345 A | | 12/2007 |
| JP | 2008-543355 A | | 12/2008 |
| JP | 2015-062733 A | | 4/2015 |
| JP | 2017-051615 A | | 3/2017 |
| JP | 2017153698 A | * | 9/2017 |
| WO | 2006/119892 A1 | | 11/2006 |

OTHER PUBLICATIONS

Dec. 6, 2023 Notice of Allowance issued in U.S. Appl. No. 17/071,050.

Mar. 6, 2025 Office Action issued in U.S. Appl. No. 17/859,491.

Tanabe et al., "A Novel Endoscopic Fundoplication for Gastroesophageal Reflux Disease; Anti-Reflux Mucosal Ablation (ARMA)," Gastrointestinal Endoscopy, 2019, vol. 89, No. 6S, p. AB190.

Sumi et al.,"Esophageal hiatal hernia and GERD: New developments in endoscopic diagnosis and treatment," Endoscopia Digestiva, May 2020, vol. 32, No. 5, pp. 707-713.

Mar. 24, 2020 International Search Report issued in International Patent Application No. PCT/JP2020/000451.

Feb. 9, 2021 International Search Report issued in International Patent Application No. PCT/JP2020/048466.

Jan. 10, 2020 Office Action issued in U.S. Appl. No. 16/279,381.

Jul. 17, 2020 Notice of Allowance issued in U.S. Appl. No. 16/279,381.

Apr. 18, 2023 Office Action issued in Japanese Patent Application No. 2021-569661.

Jun. 6, 2025 Office Action issued in Chinese Patent Application No. 202080092098.1.

Jul. 8, 2025 Office Action issued in U.S. Appl. No. 17/859,491.

Mar. 12, 2026 Office Action issued in Chinese Patent Application No. 202080092098.1.

* cited by examiner

ENDOSCOPIC TREATMENT DEVICE AND ENDOSCOPIC TREATMENT METHOD

This application is a continuation application of PCT International Application No. PCT/JP2020/000451, filed Jan. 9, 2020. The content of the PCT International Application is incorporated herein by reference.

TECHNICAL FIELD

The present disclosure relates to an endoscopic treatment device and an endoscopic treatment method.

BACKGROUND ART

As a treatment with respect to the gastroesophageal reflux disease (GERD), an oral treatment of a gastric acid secretion inhibitor and a surgical operations such as a laparoscopic Nissen fundoplication or the like are known. The Oral treatment is not a radical cure, and it is necessary to continue taking the inhibitor for a long period of time, and there may be a case in which the symptoms does not improve. The surgical operations can be expected to realize the radical cure, however, it is more invasive. Since the GERD is not a malignant disease such as a tumor or the like, it is desirable that the invasion associated with the treatment is as small as possible.

Various endoscopic treatments are being considered as options other than the oral treatment and the surgical treatment. According to one endoscopic treatment procedure, the mucosa near the gastroesophageal junction is resected such that a scar is generated at the resection site and the resection site is narrowed. As a result, the reflux of the gastric contents is suppressed.

SUMMARY

According to an aspect of the present disclosure, a treatment device includes a first pipeline that is made of material having electrical insulation, and includes an internal space; an electrode that is energizable with high frequency current; a distal-end tip that is attached to a distal end of the first pipeline, and includes a distal-end opening in communication with the internal space of the first pipeline; and a second pipeline through which liquid can pass. The second pipeline has an outer diameter smaller than an inner diameter of the first pipeline and is inserted through the first pipeline. The electrode is inserted through the second pipeline and is advanceable and retractable with respect to the second pipeline. A distal end of the electrode can be accommodated inside the second pipeline by retracting the electrode with respect to the second pipeline.

According to another aspect of the present disclosure, a treatment device includes a first pipeline that is made of material having electrical insulation and includes an internal space through which inert gas can pass; a second pipeline inserted through the first pipeline and through which liquid can pass; a distal-end tip that is attached to a distal end of the first pipeline and includes a distal-end opening in communication with the internal space such that the inert gas can be discharged through the distal-end opening; and an electrode disposed inside the distal-end tip and energizable with high frequency current.

According to a further aspect of the present disclosure, an endoscopic treatment method includes advancing an electrode with respect to a first pipeline so as to protrude a distal end of the electrode out from a distal-end opening of the first pipeline; puncturing a treatment target with a distal end of a second pipeline protruding out from the distal-end opening of the first pipeline in a state in which the distal end of the electrode is protruded out from the distal-end opening of the first pipeline; and performing a local injection from the distal end of the second pipeline to the treatment target in a state in which the distal end of the second pipeline is protruded out from the distal-end opening.

DESCRIPTION OF EMBODIMENTS

An exemplary embodiment of the present disclosure will be described with reference to FIG. 1 to FIG. 21.

Endoscopic Treatment System 300

Figure 1:
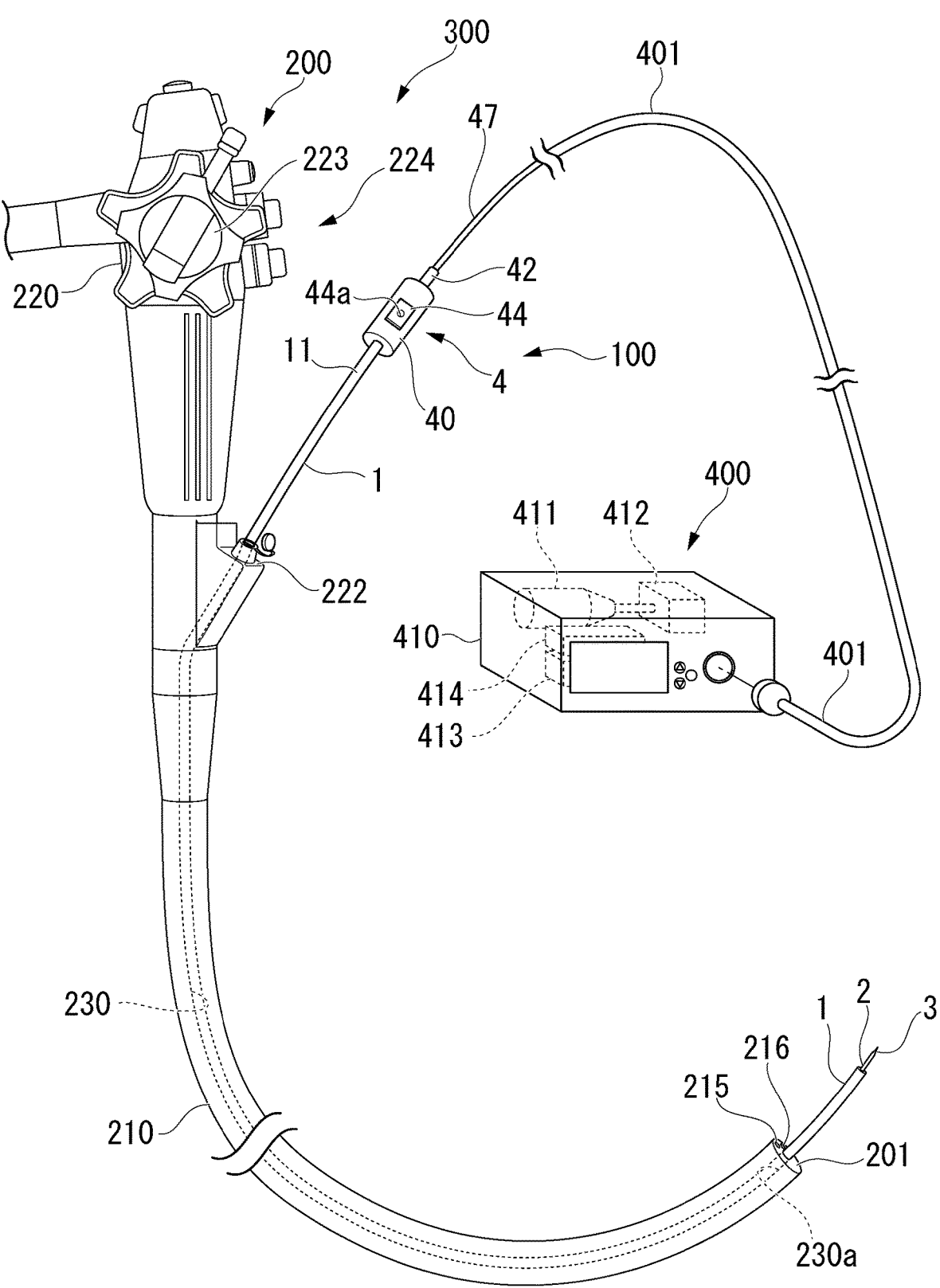
FIG. 1 is a view showing an overall configuration of an endoscopic system including a treatment device according to an exemplary embodiment of the present disclosure.

FIG. 1 is a view showing an overall configuration of an endoscopic treatment system 300 including a treatment device 100 according to the present embodiment. The endoscopic treatment system 300 includes an endoscope 200 and a treatment device 100 inserted through a channel of the endoscope 200.

Endoscope 200

The endoscope 200 is a well-known flexible endoscope, and the endoscope 200 includes an elongated insertion portion 210 and an operation portion 220 provided at a proximal-end portion of the insertion portion 210. An imaging unit 216 having a light guide 215 and a CCD or the like is provided at the distal-end portion 201 of the insertion portion 210.

The insertion portion 210 is formed with a treatment device channel 230 for inserting an endoscopic treatment device such as the treatment device 100. A distal-end portion 230a of the treatment device channel 230 is open at a distal-end portion 201 of the insertion portion 210. A proximal-end portion of the treatment device channel 230 extends to the operation portion 220.

The insertion portion 210 is configured to be freely bendable in the up-down vertical direction and the right-left horizontal direction. A distal end of the operation wire is fixed to the distal end side of the insertion portion 210. The operation wire extends through the insertion portion 210 to the operation portion 220.

On a proximal end side of the operation portion 220, a knob 223 for operating the operation wire and a switch 224 for operating the imaging unit 216 and the like are provided. The user can bend the insertion portion 210 in a desired direction by operating the knob 223.

A forceps port 222 communicating with the treatment device channel 230 is provided on the distal end side of the operation portion 220. The user can insert the endoscopic treatment device such as the treatment device 100 from the forceps port 222.

As shown in FIG. 1, the treatment device 100 can be attached to a treatment device driving device 400 via a connector 401. The treatment device driving device 400 includes, in a housing 410, a compressed gas source 411 filled with inert gas such as the argon gas or the like, a pressure regulator 412 configured to adjust the pressure of the inert gas supplied from the compressed gas source 411 so as to supply to the treatment device 100, a high-frequency power supply 413 configured to generate a high-frequency current supplied to the treatment device 100, and a controller 414 for controlling all the configurations in an integrated manner.

Treatment Device 100

Figure 2:
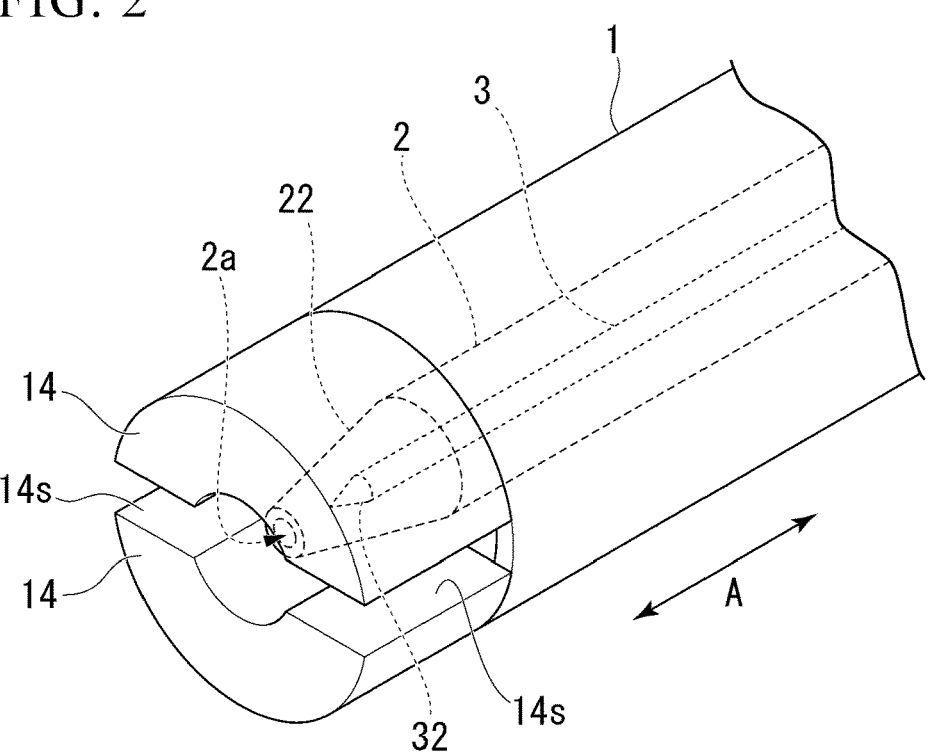
FIG. 2 is a perspective view of a distal-end portion of the treatment device.
Figure 3:
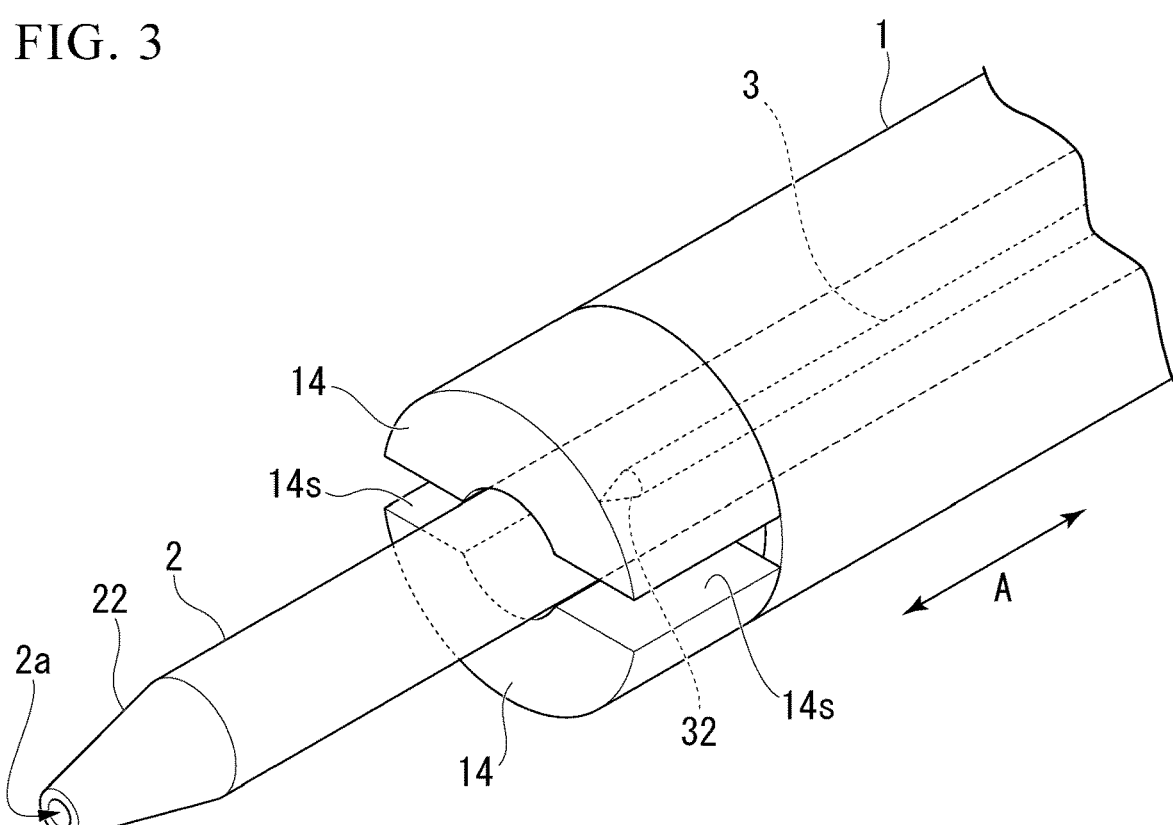
FIG. 3 is a perspective view of a distal-end portion of the treatment device.
Figure 4:
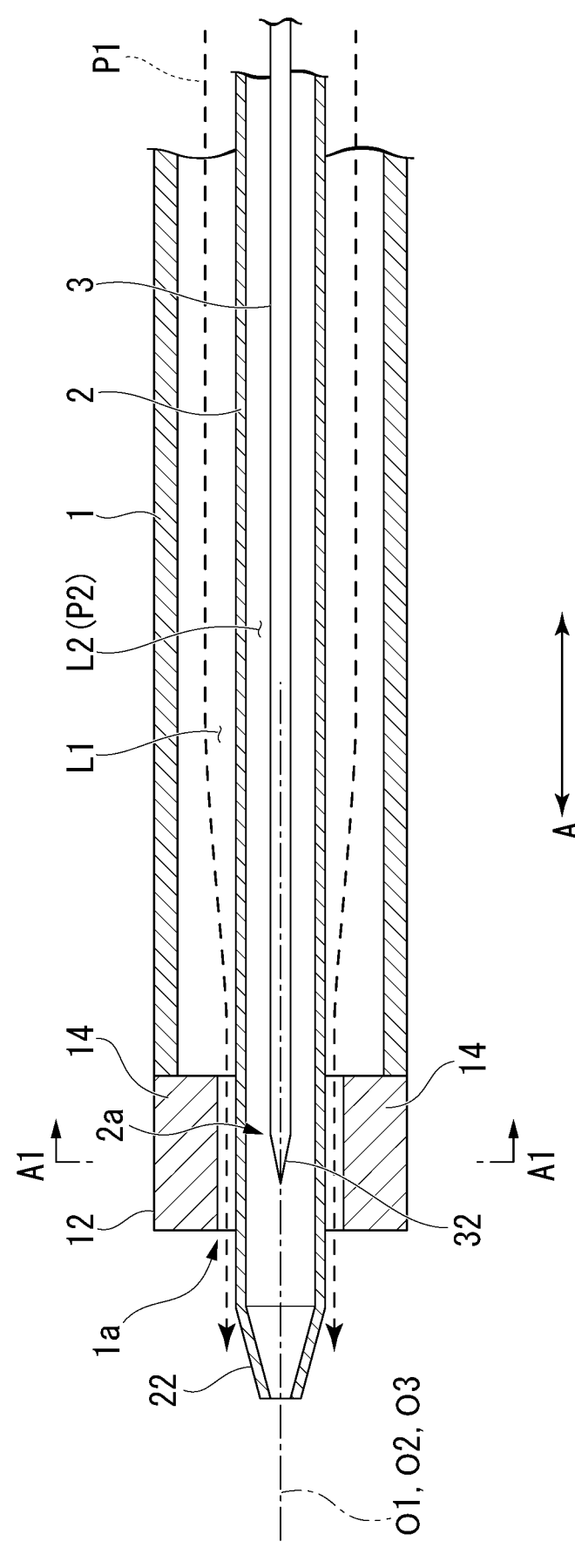
FIG. 4 is a cross-sectional view of the distal-end portion of the treatment device.
Figure 5:
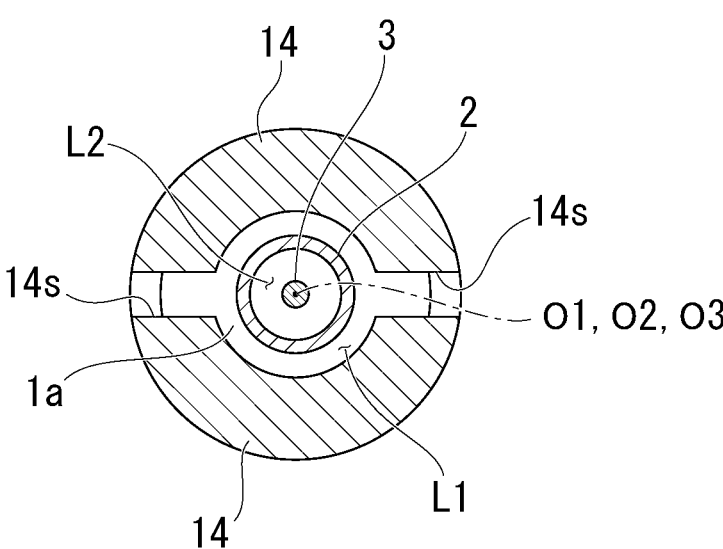
FIG. 5 is a cross-sectional view along an A1-A1 cross section.

FIG. 2 is a perspective view of the distal end portion of the treatment device 100. FIG. 3 is a perspective view of the distal end portion of the treatment device 100 in which the distal end portion 22 of the water-supply pipeline 2 projects from the gas pipeline 1. FIG. 4 is a cross-sectional view showing the distal end portion of the treatment device 100. FIG. 5 is a cross-sectional view along the cross section A1-A1 in FIG. 4. The treatment device 100 is formed in an elongated shape as a whole, and includes a gas pipeline 1, a water-supply pipeline 2, an electrode 3, and an operation portion 4.

As shown in FIG. 4, the gas pipeline (first pipeline) 1 is a tubular member having an outer diameter that can be inserted through the treatment device channel 230 of the endoscope 200. The tubular member is elongated and flexible. The internal space L1 of the gas pipeline 1 is a part of the gas flow path P1 through which the inert gas such as the argon gas flows. The gas pipeline 1 is formed from a material having electrical insulation such as the PTFE (Poly Tetra Fluoro Ethylene) or the like. The proximal-end portion 11 of the gas pipeline 1 is attached to the operation portion 4.

The gas pipeline 1 has a first opening (distal-end opening) 1a at the distal-end portion 12. The first opening 1a opens in an axial direction A of the treatment device 100. The first opening 1a communicates with the internal space L1 such that the inert gas can be discharged. The inert gas injected from the proximal-end portion 11 of the gas pipeline 1 flows through the internal space L1 of the gas pipeline 1 and is discharged from the first opening 1a of the distal-end portion 12 of the gas pipeline 1.

The water supply pipe (second pipeline) 2 has an outer diameter smaller than the inner diameter of the gas pipeline 1. As shown in FIG. 4, the water supply line (second pipeline) 2 is an elongated tubular member, and is inserted into the internal space L1 of the gas pipeline 1 so as to be relatively movable therein. The internal space L2 of the water-supply pipeline 2 is a part of the water-supply flow path P2 through which a liquid such as the physiological saline or the like flows. The water-supply pipeline 2 is made of a soft material such as the PTFE (Poly Tetra Fluoro Ethylene) and has the flexibility.

The proximal-end portion 21 of the water-supply pipeline 2 is attached to the operation portion 4, and the water-supply pipeline 2 can be advanced and retracted with respect to the gas pipeline 1 in the axial direction A of the treatment device 100 by the operations of the operation portion 4. The distal-end portion 22 of the water-supply pipeline 2 freely advances and retreats between a first position at the distal side of the gas pipeline 1 and a second position in the internal space L1 of the gas pipeline 1 (preferably in the distal-end tip 14 described later). That is, the distal-end portion 22 of the water-supply pipeline 2 can be moved to the first position by projecting the distal-end portion 22 of the water-supply pipeline 2 from the first opening 1a of the gas pipeline 1. Also, the distal-end portion 22 of the water-supply pipeline 2 can be moved to the second position by retracting the distal-end portion 22 of the water-supply pipeline 2 into the internal space L1 of the gas pipeline 1.

The proximal-end portion 11 of the gas pipeline 1 is fixed to the operation portion 4. As shown in FIG. 4, a distal-end tip 14 through which the water-supply pipeline 2 can be inserted is attached to the distal-end portion 12 of the gas pipeline 1. The inner diameter of the distal-end tip 14 is smaller than the inner diameter of the internal space L1 of the gas pipeline 1 and larger than the outer diameter of the water-supply pipeline 2. Also, as shown in FIG. 5, the central axis O2 of the water-supply pipeline 2 substantially coincides with the central axis O1 of the gas pipeline 1. Therefore, the water-supply pipeline 2 can freely advance and retract in the axial direction A in the distal-end tip 14.

As shown in FIG. 4, even in the state in which the water-supply pipeline 2 is inserted through the distal-end tip 14, there is a gap between the outer peripheral surface of the water-supply pipeline 2 and the inner peripheral surface of the distal-end tip 14. Therefore, the gap becomes a part of the gas flow path P1.

As shown in FIG. 2 and FIG. 5, a pair of slits 14s are formed on both sides of the distal-end tip 14 with the central axis O1 sandwiched therebetween. Also, the first opening 1a is formed in the distal-end tip 14. The slit 14s communicates with the first opening 1a and the internal space L1. The inert gas injected from the proximal-end portion 11 of the gas pipeline 1 passes through the internal space L1 of the gas pipeline 1 and is also discharged from the slit 14s.

The water-supply pipeline 2 has a second opening 2a at the end of the distal-end portion 22. The second opening 2a communicates with the internal space L2. The distal-end portion 22 of the water-supply pipeline 2 is formed in a shape (tapered shape) in which the outer diameter gradually decreases from the proximal end of the water-supply pipeline 2 toward the second opening 2a. The liquid injected from the proximal-end portion 21 of the water-supply pipeline 2 flows through the internal space L2 of the water-supply pipeline 2 and is discharged from the second opening 2a of the distal-end portion 22 of the water-supply pipeline 2.

As shown in FIG. 2 to FIG. 4, the electrode 3 is a wire-shaped member, and is inserted into the internal space L2 of the water-supply pipeline 2 passing through the gas pipeline 1 so as to be relatively movable. The electrode 3 is made of a metal material, has conductivity, and can be energized with a high-frequency current. The outer diameter of the electrode 3 is, for example, about 0.3 mm. The distal-end portion 32 of the electrode 3 is formed in a needle shape and functions as a "puncture needle". The most proximal end of the proximal-end portion 31 of the electrode 3 is connected to a high-frequency power supply 413 that supplies a high-frequency current.

The material of the electrode 3 is preferably a material having flexibility and elasticity so as to easily restore to the linear state even if it is bent by an external force. For example, as the material of the electrode 3, an alloy material such as a stainless alloy, a nickel-titanium alloy, a cobalt-chromium alloy, a tungsten, a tungsten alloy or the like can be adopted.

The outer diameter of the electrode 3 is smaller than the inner diameter of the water-supply pipeline 2. Also, the outer diameter of the electrode 3 is slightly smaller than the inner diameter of the second opening 2a of the water-supply pipeline 2. The electrode 3 is freely advanceable and retractable in the axial direction A along the second opening 2a. Therefore, by advancing and retreating the electrode 3 with respect to the water-supply pipeline 2, the distal-end portion 32 of the electrode 3 can be protruded from and retracted into the second opening 2a of the distal-end portion 22 of the water-supply pipeline 2. Also, as shown in FIG. 5, the central axis O3 of the electrode 3 guided to the second opening 2a of the water-supply pipeline 2 substantially coincides with the central axis O2 of the water-supply pipeline 2.

A handle (not shown) is fixed to the proximal-end portion 31 of the electrode 3. By operating the handle, the electrode 3 can be advanced and retracted with respect to at least one of the gas pipeline 1 and the water-supply pipeline 2 in the axial direction A. For example, by advancing the electrode 3 with respect to the gas pipeline 1, the distal end of the electrode 3 protrudes from the distal-end opening 1a of the distal-end tip 14. Also, by retracting the electrode 3 with respect to the gas pipeline 1, the distal end of the electrode 3 is accommodated in the gas pipeline 1, more preferably in the distal-end tip 14.

As described above, the electrode 3 is relatively free to advance and retract with respect to the gas pipeline 1 and the water-supply pipeline 2, and the water-supply pipeline 2 is also arranged so as to be relatively free to advance and retract with respect to the gas pipeline 1. That is, either of the gas pipeline 1 and the water-supply pipeline 2 can freely advance and retract relative to the electrode 3.

Figure 6:
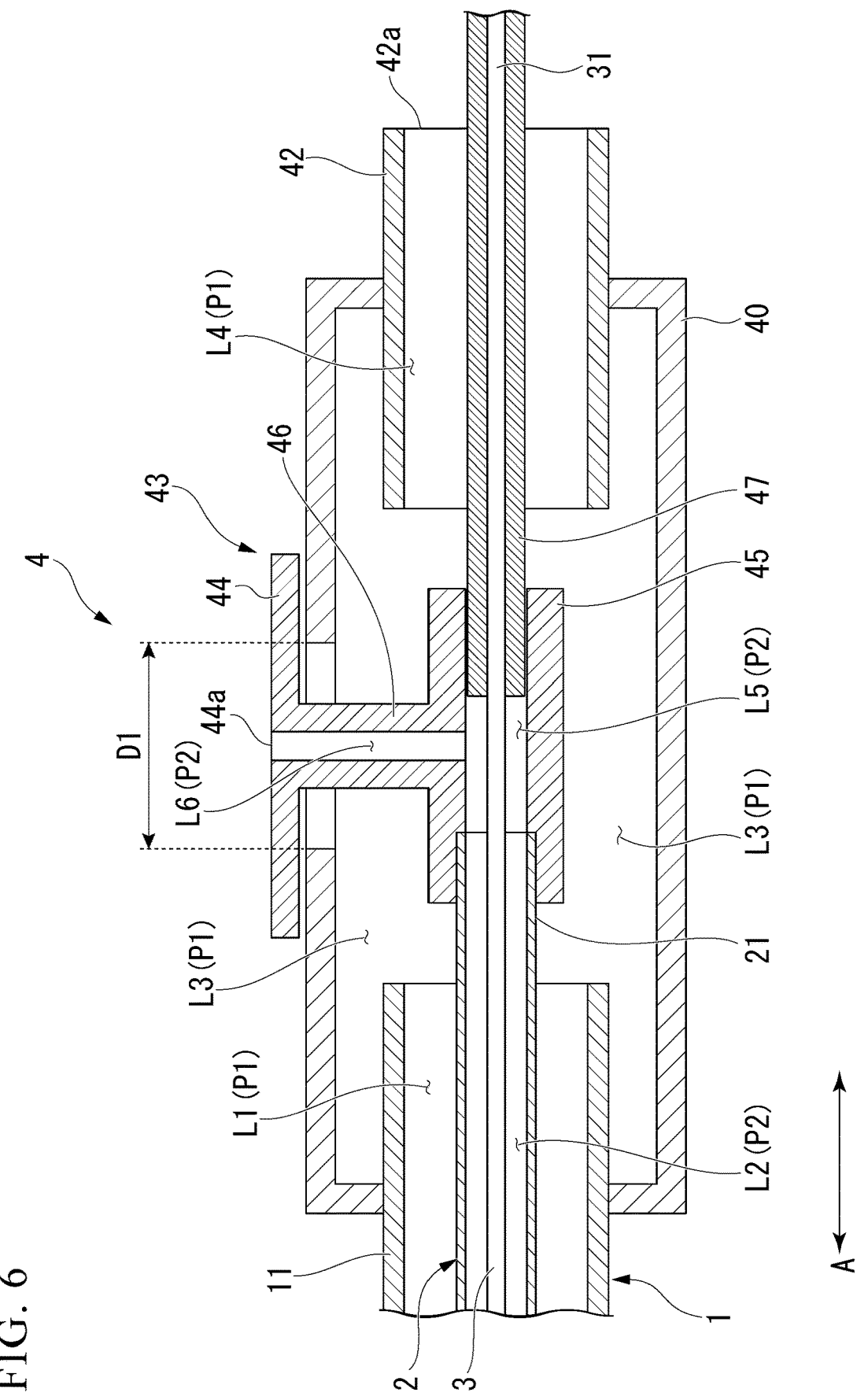
FIG. 6 is a cross-sectional view showing an operation portion of the treatment device.

FIG. 6 is a cross-sectional view showing the operation portion 4.

The operation portion 4 has an operation portion main body 40 to which the proximal-end portion 11 of the gas pipeline 1 is connected, a gas supply pipeline 42, and a slider 43.

The distal end portion of the operation portion main body 40 is fixed to the proximal-end portion 11 of the gas pipeline 1. The proximal-end portion of the operation portion main body 40 is fixed to the gas supply pipeline 42. The internal space L3 of the operation portion main body 40 communicates with the internal space L1 of the gas pipeline 1 and the internal space L4 of the gas supply pipeline 42.

The gas supply pipeline 42 is a pipeline that supplies inert gas such as the argon gas or the like to the internal space L3 of the operation portion main body 40 and the internal space L1 of the gas pipeline 1 via the internal space L4. The gas supply pipeline 42 has a gas supply port 42a on the proximal end side.

The slider 43 is attached to the operation portion main body 40 so as to be freely advanceable and retractable in the axial direction A. The slider 43 is attached to the proximal-end portion 21 of the water-supply pipeline 2. By advancing and retreating the slider 43 with respect to the operation portion main body 40 in the axial direction A, the surgeon can advance and retreat the water-supply pipeline 2 with respect to the gas pipeline 1 along the axial direction A.

The slider 43 has a water-supply pipeline 45, a support column portion 46 connected to the water-supply pipeline 45, and a handle portion 44 connected to the support column portion 46. The water-supply pipeline 45 is arranged inside the operation portion main body 40. The handle portion 44 is arranged outside the operation portion main body 40.

The water-supply pipeline 45 is formed in a cylindrical shape, and an internal space L5 is formed along the axial direction A. A distal end side of the water-supply pipeline 45 is fixed to the proximal-end portion 21 of the water-supply pipeline 2. The internal space L5 of the water-supply pipeline 45 communicates with the internal space L2 of the water-supply pipeline 2.

The electrode 3 penetrates the internal space L5 of the water-supply pipeline 45. The proximal-end portion 31 of the electrode 3 extending from the proximal end of the water-supply pipeline 45 passes through the internal space L3 of the operation portion main body 40 and the internal space L4 of the gas supply pipe 42 and extends to the outside of the operation portion 4. A cover member 47 having an insulating property such as rubber or the like is attached to the outer periphery of the proximal-end portion 31 of the electrode 3 from the proximal-end portion of the water-supply pipeline 45 to the most proximal end of the proximal-end portion 31 of the electrode 3. The most proximal end of the proximal-end portion 31 of the electrode 3 does not necessarily have to extend to the high-frequency power supply 413. For example, the most proximal end of the proximal-end portion 31 of the electrode 3 may be located inside the operation portion 4. In this case, a configuration of connecting the high-frequency power supply 413 by another metal wire via a plug or the like electrically connected to the most proximal end of the proximal-end portion 31 of the electrode 3 may be adopted.

As shown in FIG. 1, the most proximal end of the proximal-end portion 31 of the electrode 3 can be connected to the high-frequency power supply 413 by being attached to the treatment device driving device 400 via the connector 401 together with the proximal end of the gas supply pipeline 42.

The support column portion 46 is, for example, a member extending in an orthogonal direction with respect to the axial direction A. When the support column portion 46 comes into contact with a part of the operation portion main body 40 located in the front-rear direction in the axial direction A, the support column portion 46 regulates an advance-retract range D1 of the slider 43.

The handle portion 44 is a member that the surgeon grasps when the surgeon advances and retracts the slider 43 with respect to the operation portion main body 40. The handle portion 44 includes a liquid-supply port 44a for supplying a liquid to the water-supply flow path P2.

The support column portion 46 has an internal space L6 that connects the liquid-supply port 44a of the handle portion 44 and the internal space L5 of the water-supply pipeline 45. The liquid-supply port 44a, the internal space L6 of the support column portion 46, the internal space L5 of the water-supply pipeline 45, and the internal space L2 of the water-supply pipeline 2 communicate with each other to form the water-supply flow path P2. The liquid supplied from the liquid-supply port 44a is discharged from the second opening 2a of the distal-end portion 22 of the water-supply pipeline 2 via the water-supply flow path P2.

Since the proximal-end side opening of the internal space L5 is sealed by the cover member 47 and the electrode 3, the liquid supplied to the internal space L5 of the water-supply pipeline 45 is discharged to the internal space L3 of the operation portion main body 40.

The gas supply port 42a, the internal space L4 of the gas supply pipeline 42, the internal space L3 of the operation portion main body 40, and the internal space L1 of the gas pipeline 1 communicate with each other to form the gas flow path P1. The inert gas supplied from the gas supply port 42a is discharged from the first opening 1a of the distal-end portion 12 of the gas pipeline 1 via the gas flow path P1.

The internal space L1 of the gas pipeline 1, the internal space L3 of the operation portion main body 40, and the internal space L4 of the gas-supply pipeline 42 are airtight by an O-ring or the like that is not shown in figures.

Effects of Endoscopic Treatment System 300

Next, the effects of the endoscopic treatment system 300 according to the present embodiment will be described. The effects of the endoscopic treatment system 300 will be described by taking an endoscopic treatment method for the gastroesophageal reflux disease (GERD) using the endoscopic treatment system 300 as an example. The endoscopic treatment method to which the endoscopic treatment system 300 is applied is not limited to this example. For example, the endoscopic treatment system 300 is also applied to an endoscopic treatment method for resecting a part of a lesion or the like.

The surgeon inserts the endoscope 200 through a natural orifice such as the mouth or the nose of the target (insertion step), and moves the distal-end portion 201 of the endoscope 200 into the stomach (gastrointestinal tract).

Figure 7:
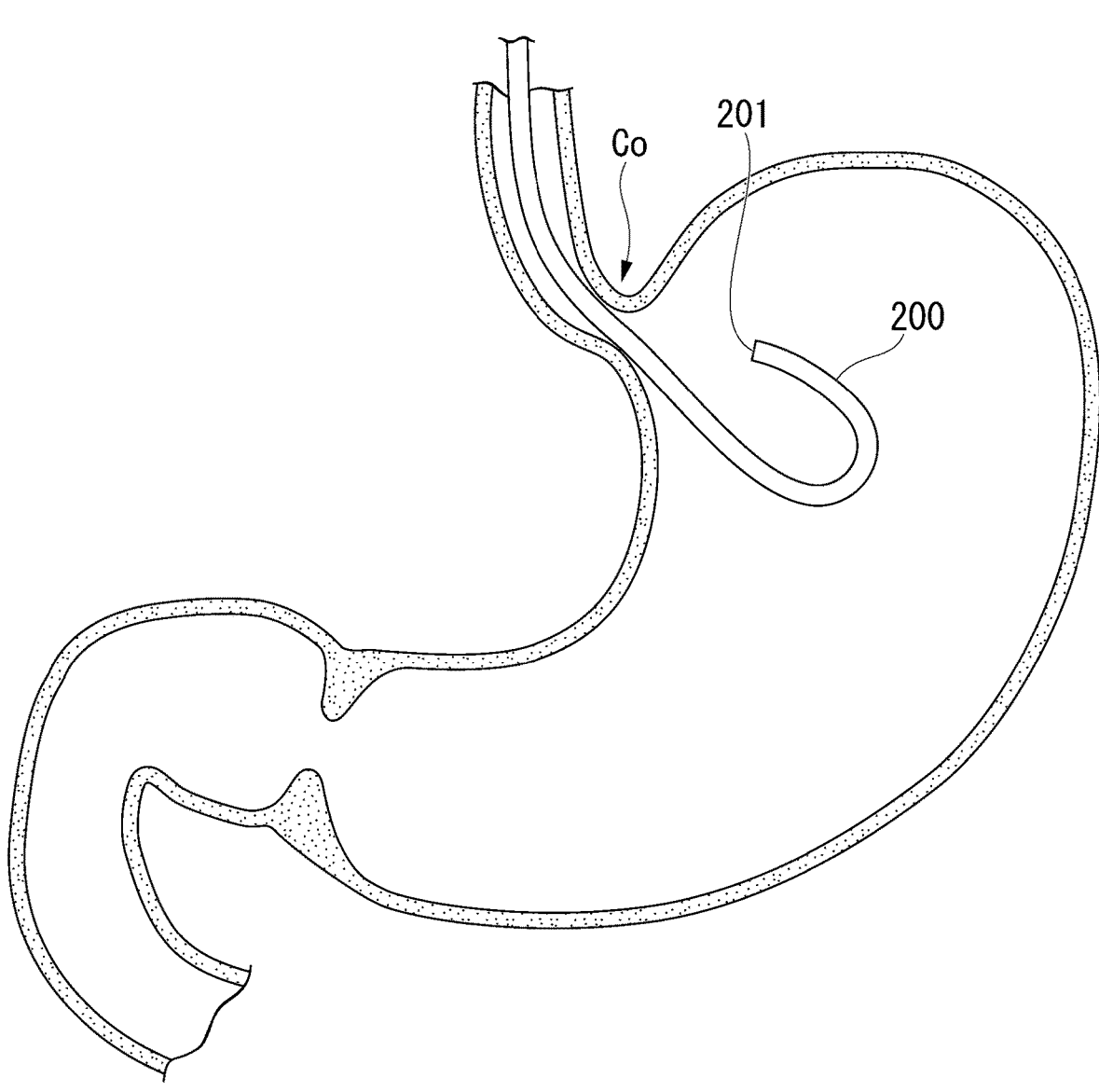
FIG. 7 is a view showing a state of observing the gastroesophageal junction by an endoscope inserted into the stomach.

FIG. 7 is a view showing a state of observing the gastroesophageal junction by the endoscope 200 inserted into the stomach.

The surgeon then bends the endoscope 200. As shown in FIG. 7, the surgeon directs the distal-end portion 201 of the endoscope 200 toward the cardia Co, and captures the gastroesophageal junction around the cardia Co within the view field of the endoscope 200. While observing the gastroesophageal junction, the surgeon identifies a treatment region R, which is the target of the local injection treatment or cauterization treatment described later (treatment region identification step).

Next, the surgeon bulges the treatment region R by performing the local injection of a liquid into the submucosal layer N of the specified treatment region R (local injection step). The liquid to be injected is the physiological saline, the sodium hyaluronate solution, the glycerin or the like.

Figure 8:
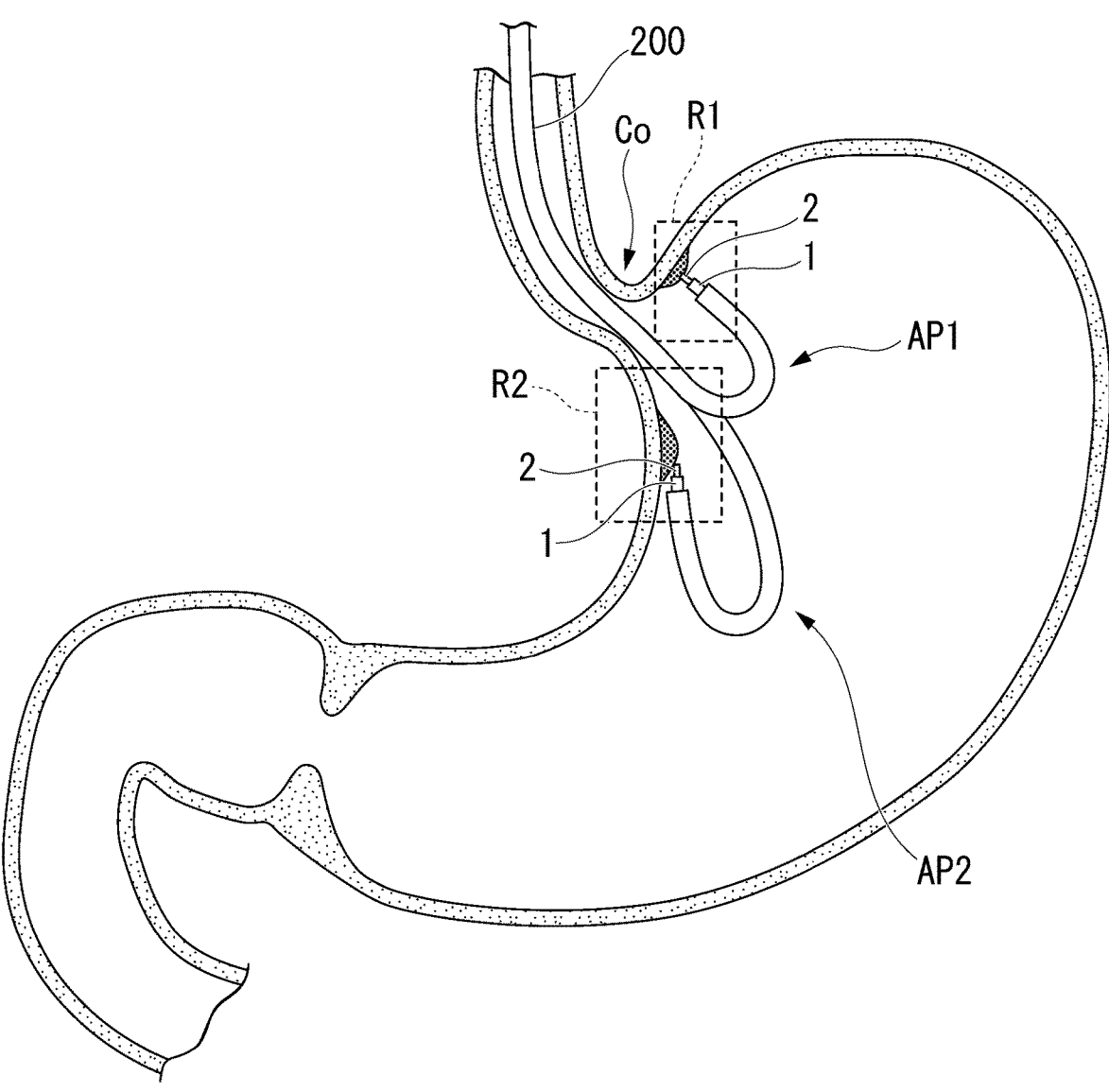
FIG. 8 is a view showing the treatment device for performing a local injection at a treatment region.
Figure 9:
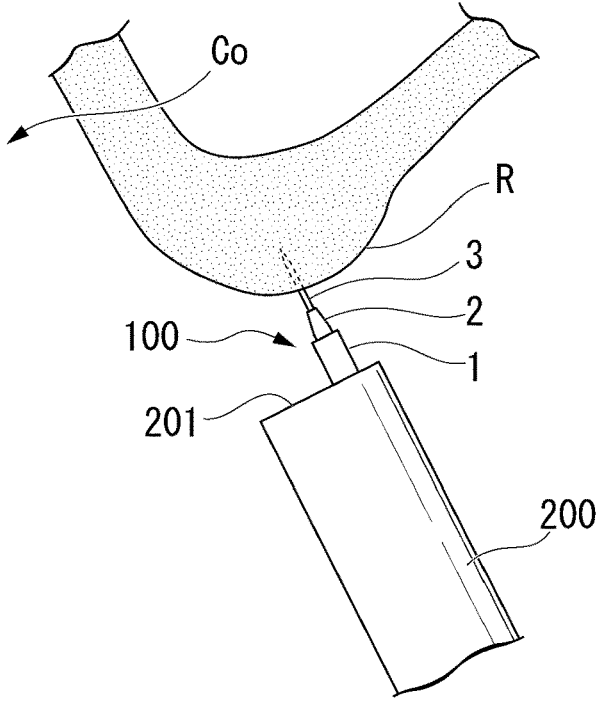
FIG. 9 is an enlarged view of a region R1 shown in FIG. 8.
Figure 10:
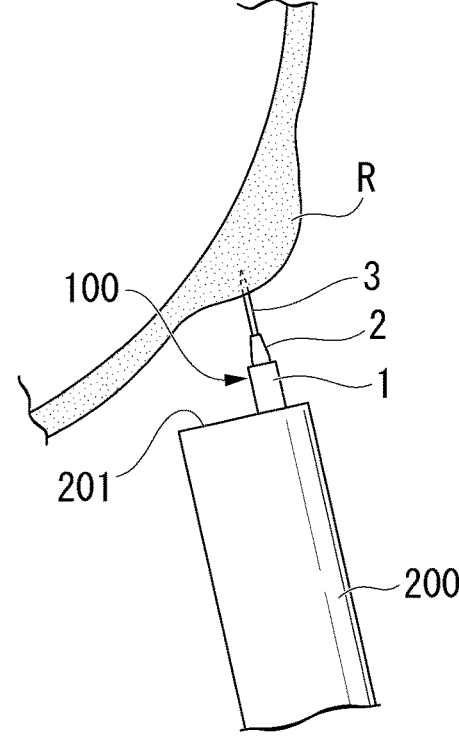
FIG. 10 is an enlarged view of a region R2 shown in FIG. 8.

FIG. 8 is a view showing a treatment device 100 configured to perform the local injection at the specified treatment region R. FIG. 9 is an enlarged view showing the region R1 (a part of the region on the greater curvature side) shown in FIG. 8. FIG. 10 is an enlarged view of the region R2 (a part of the region on the lesser curvature side) shown in FIG. 8.

The local injection methods at the treatment region R at least include a frontal approach AP1 and a tangential approach AP2. In the frontal approach AP1, the surgeon arranges the treatment device 100 at a position where the distal-end portion 12 of the gas pipeline 1 faces the treatment region R by operating the treatment device 100 or the distal-end portion 201 of the endoscope 200. In the tangential approach AP2, the treatment device 100 is arranged at a position where the side portion of the distal-end portion 12 of the gas pipeline 1 faces the treatment region R.

FIG. 11 to FIG. 15 are cross-sectional views of the distal-end portion of the treatment device 100 at the time of performing the local injection of the liquid.

Figure 11:
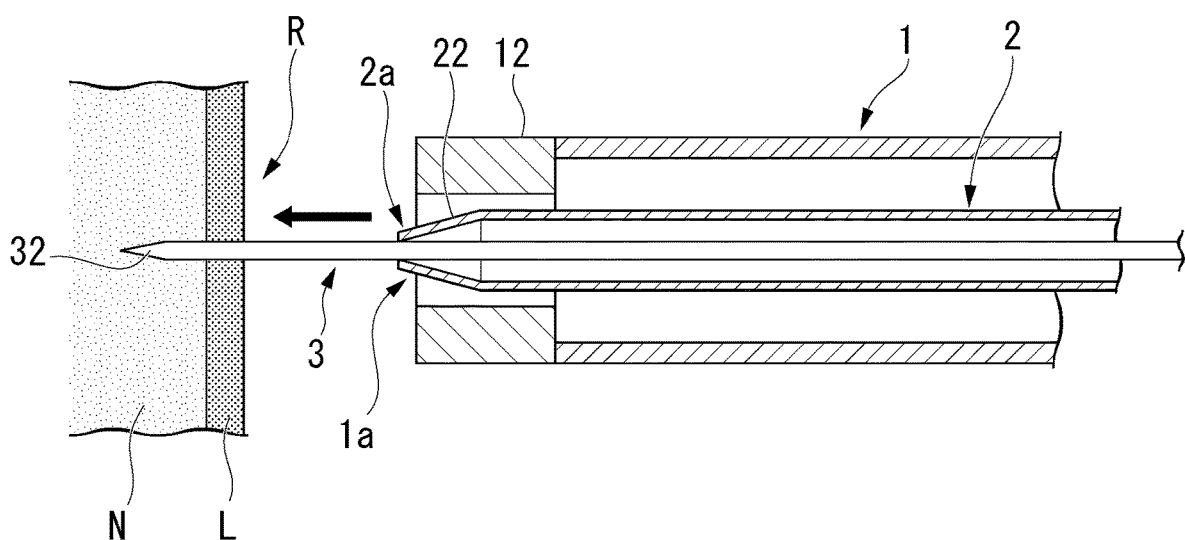
FIG. 11 is a cross-sectional view showing a distal-end portion of the treatment device when performing the local injection.

As shown in FIG. 11, the surgeon causes the electrode 3 to protrude from the first opening 1a and the second opening 2a by advancing the electrode 3 relative to the gas pipeline 1 and the water-supply pipeline 2 (first state). The surgeon punctures the distal-end portion 32 of the electrode 3 into the treatment region R and advances the electrode 3 until the distal-end portion 32 of the electrode 3 penetrates the mucosal layer L and reaches the submucosal layer N.

Figure 12:
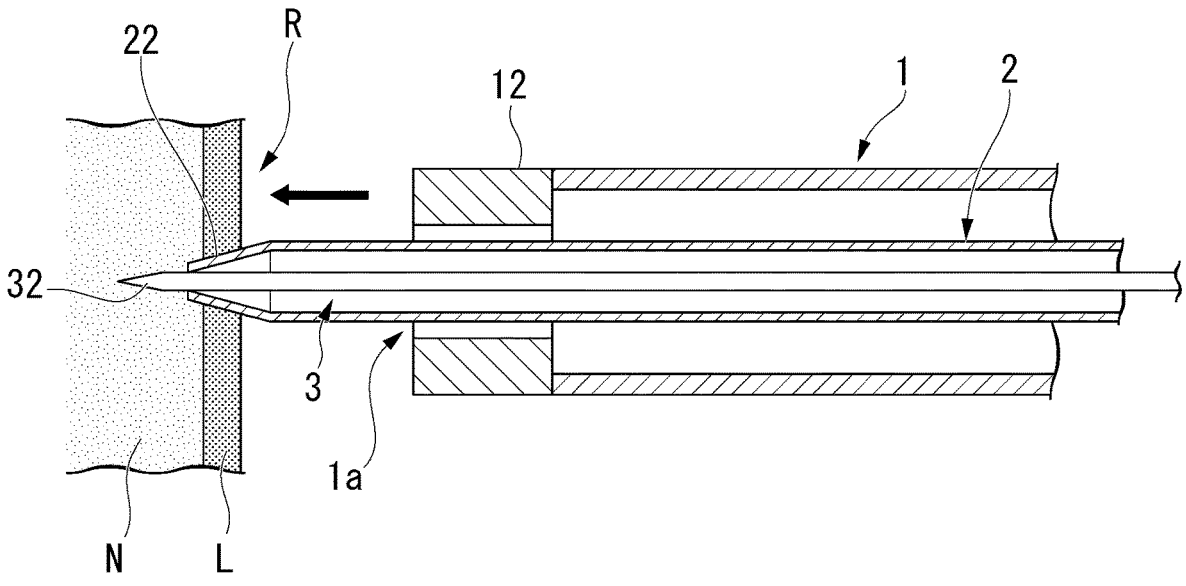
FIG. 12 is a cross-sectional view showing the distal-end portion of the treatment device when performing the local injection.

The surgeon advances the water-supply pipeline 2 relative to the gas pipeline 1 by advancing the slider 43 with respect to the operation portion main body 40. Then, as shown in FIG. 12, the distal-end portion 22 of the water-supply pipeline 2 is projected from the first opening 1a of the gas pipeline 1. By this operation, the distal-end portion 22 of the water-supply pipeline 2 is moved to the first position. By moving the slider 43 to the most advanced side of the advance-retract range D1, the surgeon can easily position the distal-end portion 22 of the water-supply pipeline 2 at the first position. The surgeon delivers the distal-end portion 22 of the water-supply pipeline 2 to the submucosal layer N by advancing the water-supply pipeline 2 along the electrode 3. Since the distal-end portion 22 of the water-supply pipeline 2 has a tapered shape, it is easy to puncture the mucosal layer L or the like.

Figure 13:
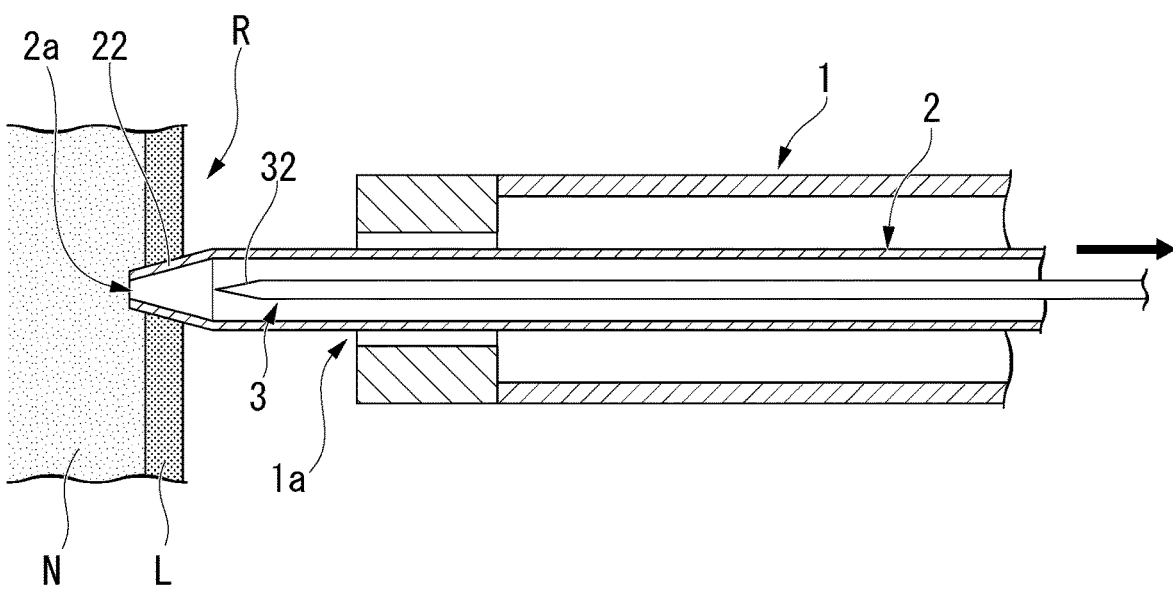
FIG. 13 is a cross-sectional view showing the distal-end portion of the treatment device when performing the local injection.

As shown in FIG. 13, the surgeon retracts only the electrode 3 with respect to the water-supply pipeline 2 without retreating the water-supply pipeline 2, such that the distal-end portion 32 of the electrode 3 is moved to the position at the proximal end side of the second opening 2a of the water-supply pipeline 2. As a result, the distal-end portion 32 of the electrode 3 is removed from the mucosal layer L and the submucosal layer N.

Figure 14:
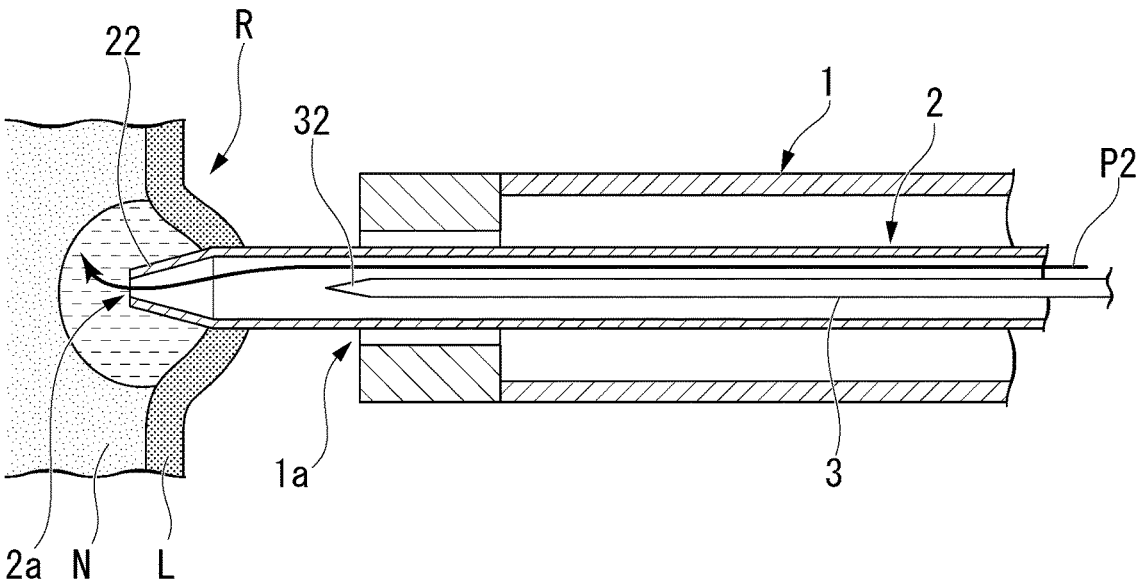
FIG. 14 is a cross-sectional view showing the distal-end portion of the treatment device when performing the local injection.

The surgeon supplies the liquid to the liquid-supply port 44a. As shown in FIG. 14, the supplied liquid is supplied from the second opening 2a of the distal-end portion 22 of the water-supply pipeline 2 via the water-supply flow path P2, and is locally injected into the submucosal layer N. As a result, the treatment region R to which the liquid is locally injected bulges. When the water pressure of the liquid is sufficiently high, the surgeon may perform the local injection of the liquid into the submucosal layer N without removing the distal-end portion 32 of the electrode 3 from the mucosal layer L and the submucosal layer N.

Figure 15:
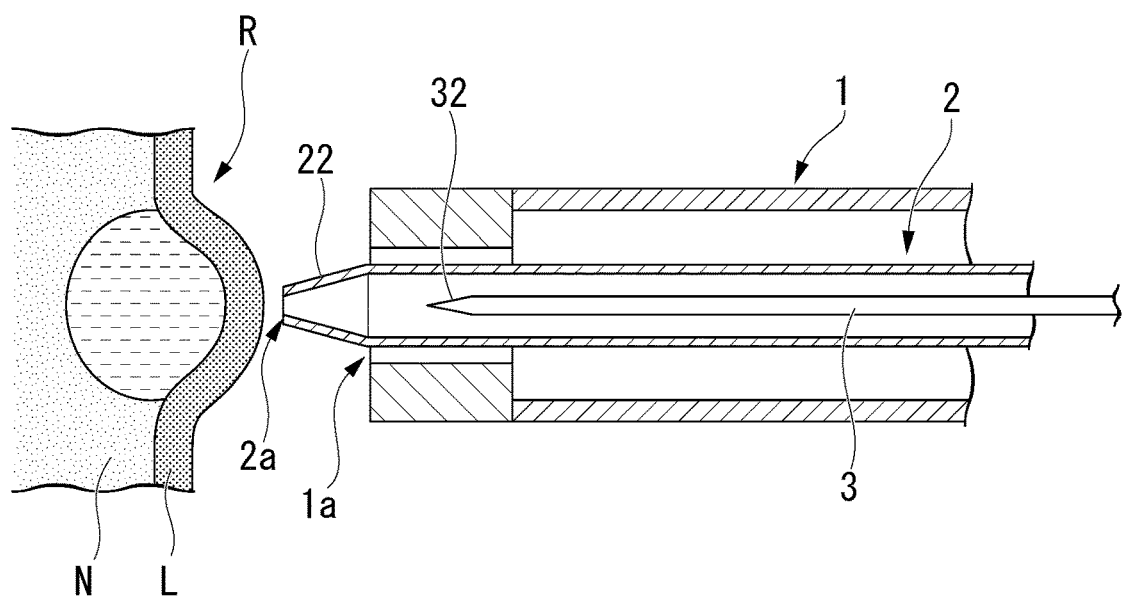
FIG. 15 is a cross-sectional view showing the distal-end portion of the treatment device when performing the local injection.

As shown in FIG. 15, the surgeon retracts the distal-end portion 22 of the water-supply pipeline 2 by retracting the slider 43 with respect to the operation portion main body 40. As a result, the distal-end portion 22 of the water-supply pipeline 2 is removed from the mucosal layer L and the submucosal layer N. The surgeon may pull out the distal-end portion 22 of the water-supply pipeline 2 from the mucosal layer L and the submucosal layer N by retracting the entire treatment device 100.

Figure 16:
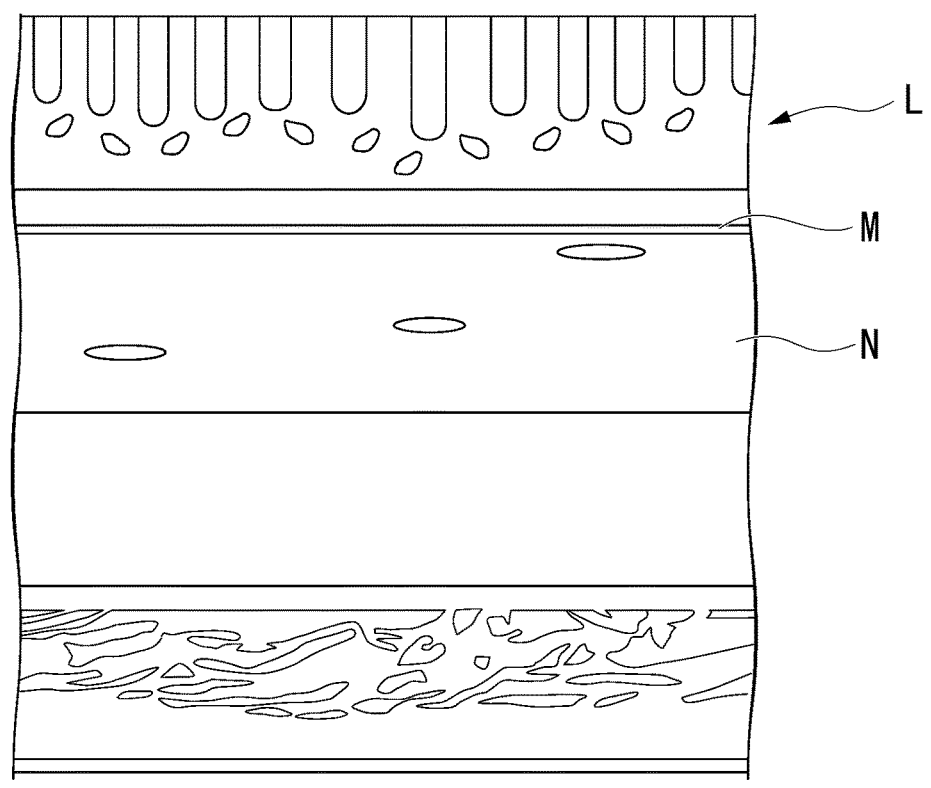
FIG. 16 is a schematic cross-sectional view of the stomach wall.

Next, the surgeon cauterizes the bulged treatment region R (cauterization step). At this time, only the cauterization is performed without resecting the mucous membrane. The degree of the cauterization is such that the mucosa basal layer M is damaged. FIG. 16 shows a schematic cross-sectional view of the stomach wall. The mucosal basal layer M is a part of the mucosal layer L and the mucosal basal layer M is a layer including a boundary surface in contact with the submucosal layer N. The mucosal basal layer M may also be referred to as a basement membrane.

Figure 17:
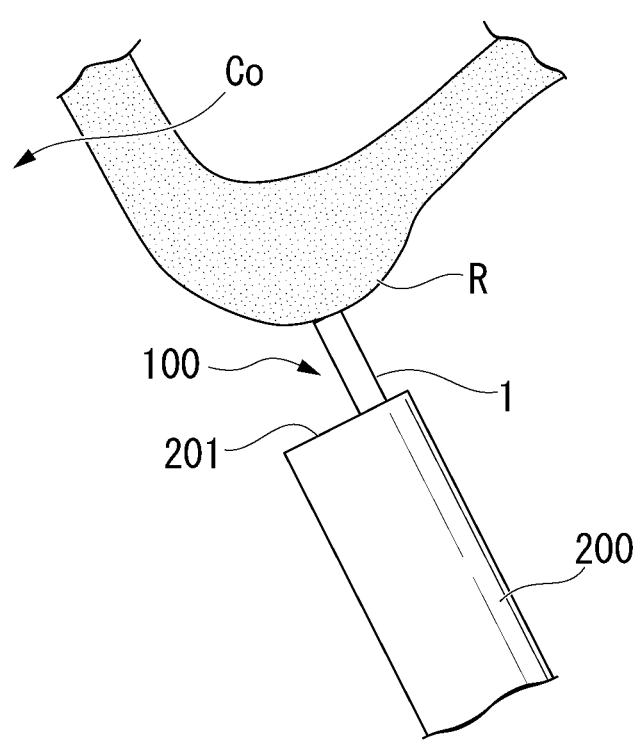
FIG. 17 is a view showing the treatment device that is deployed at a position to cauterize the treatment region by a frontal approach.

FIG. 17 is an enlarged view of the region R1 shown in FIG. 8 and is a view showing the treatment device 100 arranged at a position where the treatment region R is cauterized by the frontal approach AP1. In the frontal approach AP1, the surgeon arranges the treatment device 100 at the position where the distal-end portion 12 of the gas pipeline 1 comes into contact with the treatment region R located in the region R1 by operating the treatment device 100 or the endoscope 200.

Figure 18:
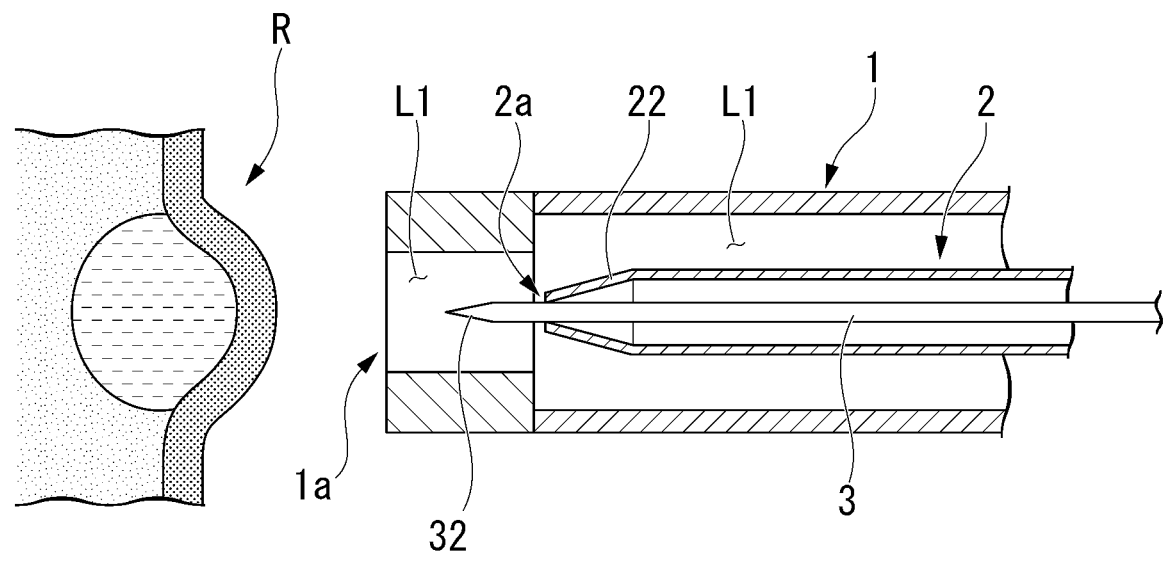
FIG. 18 is a cross-sectional view showing the distal-end portion of the treatment device when cauterizing the treatment region.
Figure 19:
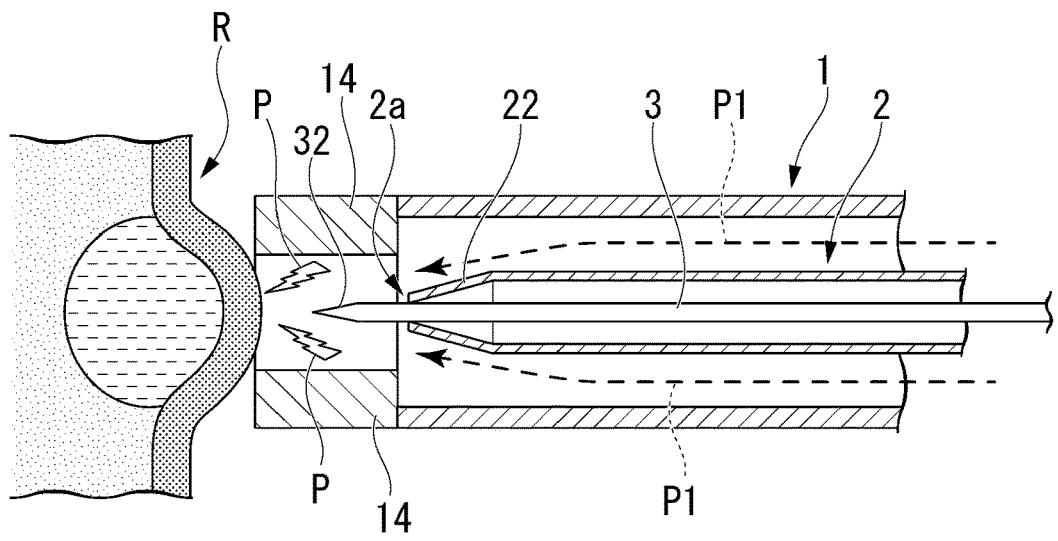
FIG. 19 is a cross-sectional view showing the distal-end portion of the treatment device when cauterizing the treatment region.

FIG. 18 and FIG. 19 are cross-sectional views showing the distal-end portion of the treatment device 100 when cauterizing the treatment region R in the frontal approach shown in FIG. 17. As shown in FIG. 18, the surgeon retracts the water-supply pipeline 2 relative to the gas pipeline 1 by retracting the slider 43 with respect to the operation portion main body 40. Then, the distal-end portion 22 of the water-supply pipeline 2 is drawn into the internal space L1 of the gas pipeline 1, more preferably inside the distal-end tip 14. By this operation, the distal-end portion 22 of the water-supply pipeline 2 is moved to the second position. The surgeon can easily position the distal-end portion 22 of the water-supply pipeline 2 at the second position by moving the slider 43 to the most proximal end of the advance-retract range D1. In addition, the surgeon retracts the electrode 3 relative to the water-supply pipeline 2 and the gas pipeline 1 by operating the handle (not shown) fixed to the proximal-end portion 31 of the electrode 3. As a result, the distal-end portion 32 of the electrode 3 is also accommodated in the gas pipeline 1, more preferably in the distal-end tip 14 (second state). By this operation, for example, as shown in FIG. 18, the surgeon moves the distal-end portion 32 of the electrode 3 to the position at the more proximal end side than the first opening 1a of the gas pipeline 1 and at the more distal end side than the second opening 2a of the water-supply pipeline 2.

The surgeon supplies the inert gas to the gas-supply port 42a in the state of positioning the distal-end portion 32 of the electrode 3 at the position at the more proximal end side than the first opening 1a of the gas pipeline 1 and at the more distal end side than the second opening 2a of the water-supply pipeline 2. As shown in FIG. 19, the supplied inert gas is discharged from the first opening 1a of the distal-end portion 12 of the gas pipeline 1 to the vicinity of the treatment region R via the gas flow path P1. The surgeon supplies a high-frequency current to the electrode 3 while supplying the inert gas. By discharging the high-frequency current in the inert gas, the inert gas is ionized and becomes plasma P. Since the plasma P has electrical conductivity, the plasma P is used as a medium to promote stable maintenance of the discharge from the distal-end portion 32 of the electrode 3 toward the treatment region R. As a result, the treatment region R is cauterized in a state where the distal-end portion 32 of the electrode 3 and the treatment region R are not in contact with each other.

Figure 20:
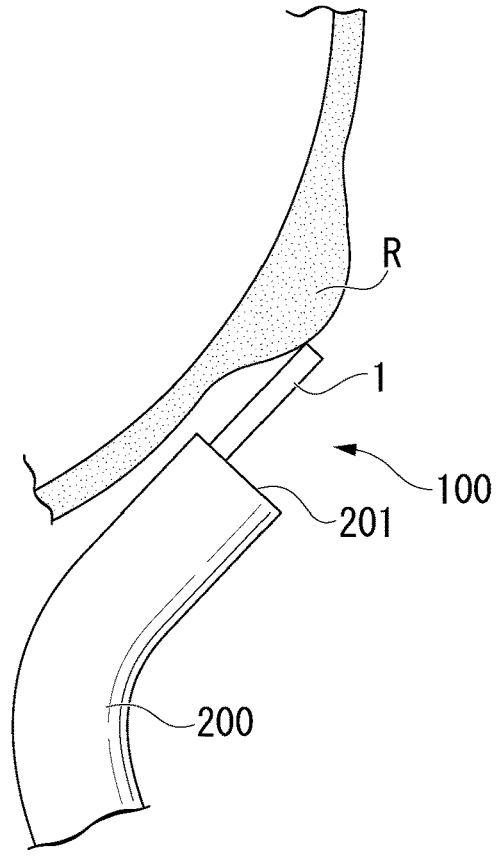
FIG. 20 is a view showing the treatment device that is deployed at a position to cauterize the treatment region by a tangential approach.

FIG. 20 is an enlarged view of the region R2 shown in FIG. 8 and is a view showing the treatment device 100 arranged at a position where the treatment region R is cauterized by the tangential approach AP2. In the tangential approach AP2, the surgeon operates the treatment device 100 or the endoscope 200 to arrange the treatment device 100 at the position where the side portion of the distal-end portion 12 of the gas pipeline 1 comes into contact with the treatment region R located in the R2 region.

Similar to the frontal approach AP1 shown in FIG. 18, in the tangential approach AP2, by the operations of the surgeon pulling the distal-end portion 22 of the water-supply pipeline 2 into the internal space L1 of the gas pipeline 1, the surgeon moves the distal-end portion 22 of the water-supply pipeline 2 to the second position. Also, the surgeon retracts the electrode 3 with respect to the water-supply pipeline 2 and the gas pipeline 1. As a result, in the tangential approach AP2 as well as the frontal approach AP1, it is possible for the surgeon to move the distal-end portion 32 of the electrode 3 to the position at the more proximal end side than the first opening 1a of the gas pipeline 1 and at the more distal end side than the second opening 2a of the water-supply pipeline 2.

Figure 21:
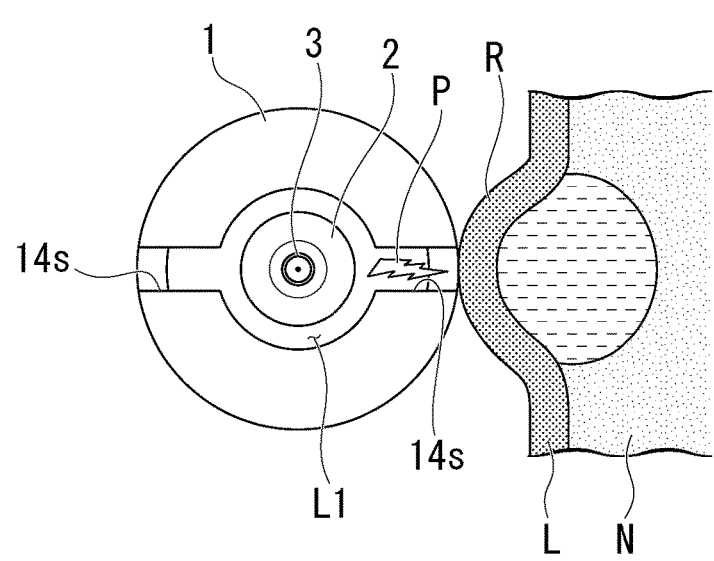
FIG. 21 is a front view showing the treatment device when cauterizing the treatment region by the tangential approach.

FIG. 21 is a front view showing the distal end portion of the treatment device 100 when cauterizing the treatment region R by the tangential approach AP2. In the tangential approach AP2, the inert gas discharged from the slit 14s at the distal-end portion 12 of the gas pipeline 1 becomes the plasma P. Since the plasma P has the electrical conductivity, the plasma P as the medium promotes stable maintenance of the discharge from the distal-end portion 32 of the electrode 3 toward the treatment region R. As a result, the treatment region R is cauterized in a state where the distal-end portion 32 of the electrode 3 and the treatment region R are not in contact with each other.

When cauterizing the treatment region R, the distal-end portion 32 of the electrode 3 is located on the proximal end side of the first opening 1a of the gas pipeline 1, preferably disposed inside the distal-end tip 14 of the gas pipeline 1. Accordingly, it is difficult for the scorching due to contact between the electrode and the tissue during the cauterization to occur. The distal-end portion 32 of the electrode 3 has the same effect even if being arranged in the internal space L1.

Since the basal layer M of the mucosa is damaged by the cauterization, the gastric mucosa of the treatment region R is subsequently regenerated through the process of scar formation. During the mucosal regeneration, the gastric mucosa surrounding the treatment region R is attracted toward the treatment region R by the contractile action of the tissue surrounding the treatment region R in the process of the scar formation when the damaged mucosa heals. By utilizing this effect, the symptom of GERD is improved by forming an incomplete stenosis in the cardia Co to prevent the reflux symptom.

When the incomplete stenosis is formed in the cardia Co, the surface area of the mucosal surface in the treatment region R where cauterization is required is large. Since the treatment device 100 that cauterizes using the inert gas and the high-frequency current has a wider range of cauterization at once than the treatment device such as the high-frequency knife or the like, it is possible to perform a quick cauterization over a wide treatment range R so as to simplify the treatment and shorten time required for the treatment.

The surgeon repeatedly performs the local injection step and the cauterization step to cauterize the treatment region R. At this time, it is unnecessary for the surgeon to remove the treatment device 100 from the treatment device channel 230 and replace it with another treatment device, and it is possible to repeat the local injection and the cauterization treatment.

Although the present embodiment has been described in detail with reference to the drawings, the specific configuration is not limited to this embodiment, and design changes and the like within a range that does not deviate from the scope of the present invention are also included. In addition, the components shown in the above-described embodiment and the modification examples shown below can be appropriately combined and configured.

For example, in the above embodiment, the water-supply pipeline 2 is inserted through the internal space L1 of the gas pipeline 1, however the configuration of the water-supply pipeline and the gas pipeline is not limited to this example. The water-supply pipeline and the gas pipeline may be provided in parallel with each other.

Figure 22:
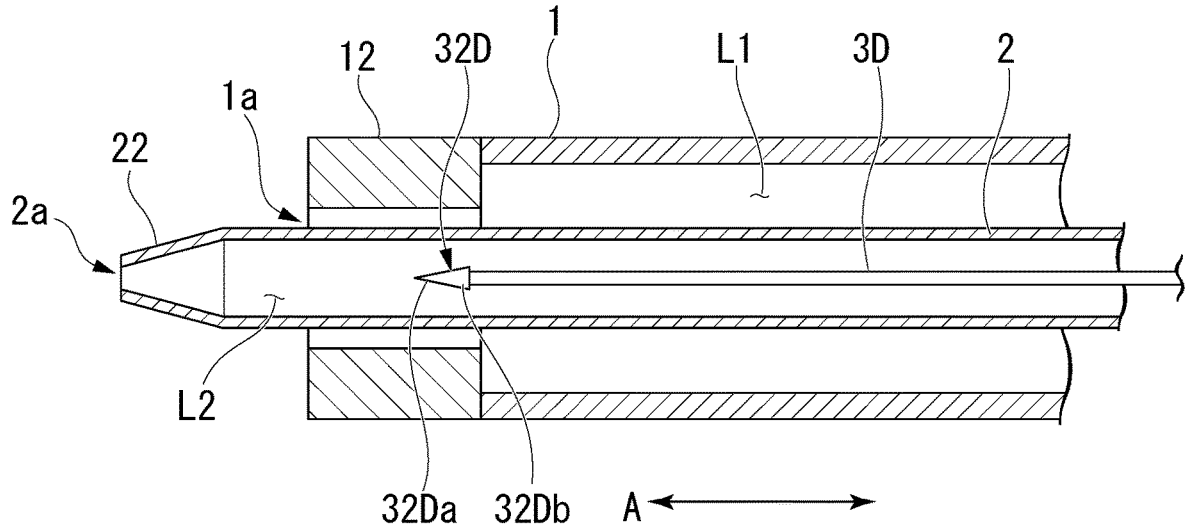
FIG. 22 is a cross-sectional view showing the distal-end portion including a modification example of the electrode.

The treatment device 100 may have an electrode 3D instead of the electrode 3. FIG. 22 is a cross-sectional view of the distal-end portion of the treatment device 100 including the electrode 3D. A proximal-end portion of the electrode 3D is attached to the operation portion 4 so as not to be advanceable and retractable in the axial direction A, and the distal-end portion of the electrode 3D is arranged in the distal-end tip 14. The distal-end portion 32D of the electrode 3D is formed in an arrowhead shape. The electrode 3D has a small diameter portion 32Da on the distal end side and a large diameter portion 32Db on the proximal end side. The outer diameter of the large diameter portion 32Db is larger than the outer diameter of the small diameter portion 32Da, and the maximum outer diameter of the large diameter portion 32Db is larger than the inner diameter of the second opening 2a of the distal-end portion 22 of the water-supply pipeline 2. On the other hand, the maximum outer diameter of the small diameter portion 32Da is smaller than the inner diameter of the second opening 2a of the distal-end portion 22 of the water-supply pipeline 2. The water-supply pipeline 2 is provided so as to be advanceable and retractable with respect to the electrode 3D.

Figure 23:
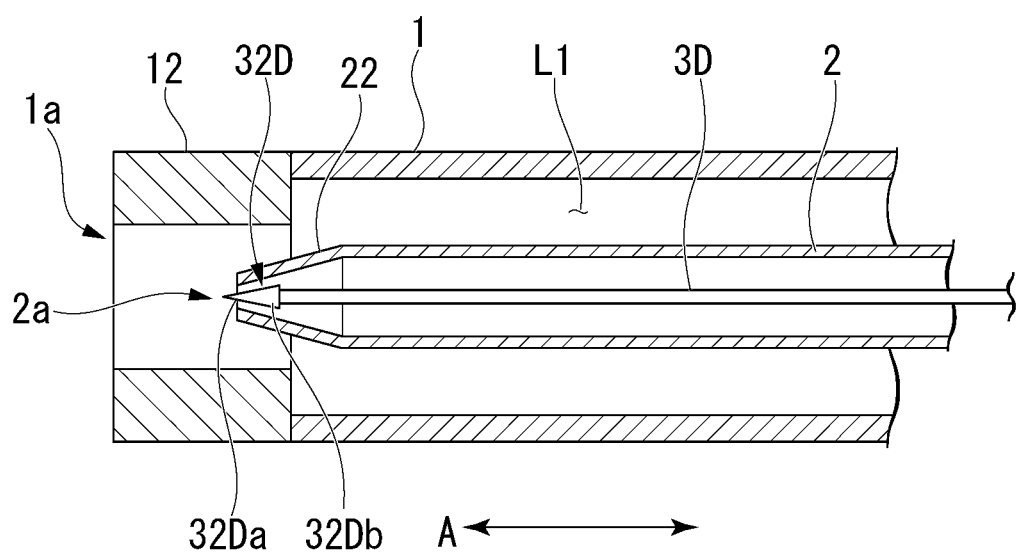
FIG. 23 is a cross-sectional view showing the distal-end portion when cauterizing the treatment region.

FIG. 23 is a cross-sectional view of the distal-end portion of the treatment device 100 when cauterizing the treatment region R.

As shown in FIG. 23, the surgeon retracts the water-supply pipeline 2 with respect to the gas pipeline 1 and the electrode 3D to bring the distal-end portion 32D of the electrode 3D into contact with the distal-end portion 22 of the water-supply pipeline 2. The maximum outer diameter of the large diameter portion 32Db at the distal-end portion 32D of the electrode 3D is larger than the inner diameter of the second opening 2a of the distal-end portion 22 of the water-supply pipeline 2. On the other hand, the maximum outer diameter of the small diameter portion 32Da is smaller than the inner diameter of the second opening 2a of the distal-end portion 22 of the water-supply pipeline 2. Therefore, the small diameter portion 32Da on the distal end side of the distal-end portion 32D of the electrode 3D protrudes from the second opening 2a of the water-supply pipeline 2.

Figure 24:
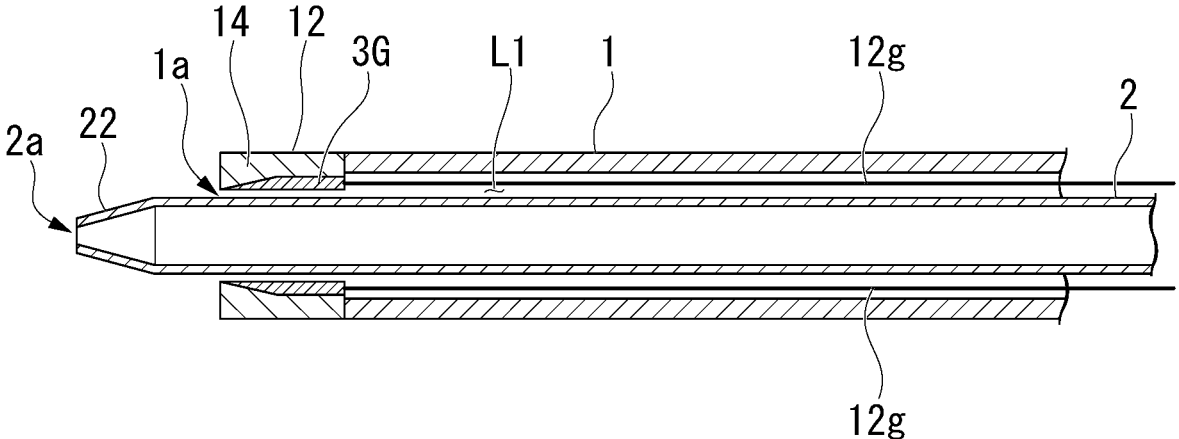
FIG. 24 is a cross-sectional view showing the distal-end portion including another modification example of the electrode.

The treatment device 100 may have an electrode 3G instead of the electrode 3. FIG. 24 is a cross-sectional view of the distal-end portion of the treatment device 100 including the electrode 3G. The electrode 3G is fixed to the inner peripheral surface of the gas pipeline 1. Specifically, the electrode 3G is fixed in the distal-end tip 14. The electrode 3G cannot advance and retract in the axial direction A, and the distal end of the electrode 3G is arranged at the proximal end side of the water-supply pipeline 2 than the distal-end portion 22 of the water-supply pipeline 2. The treatment device 100 can cauterize the treatment region R in a state where the distal-end portion of the electrode 3G and the treatment region R do not come into contact with each other. The electrode 3G is connected to a high frequency power supply 413 that supplies a high frequency current via a wire 12g. The electrode 3G may be fixed to the outer peripheral surface of the water-supply pipeline 2 in the internal space L1 of the gas pipeline 1.

Figure 25:
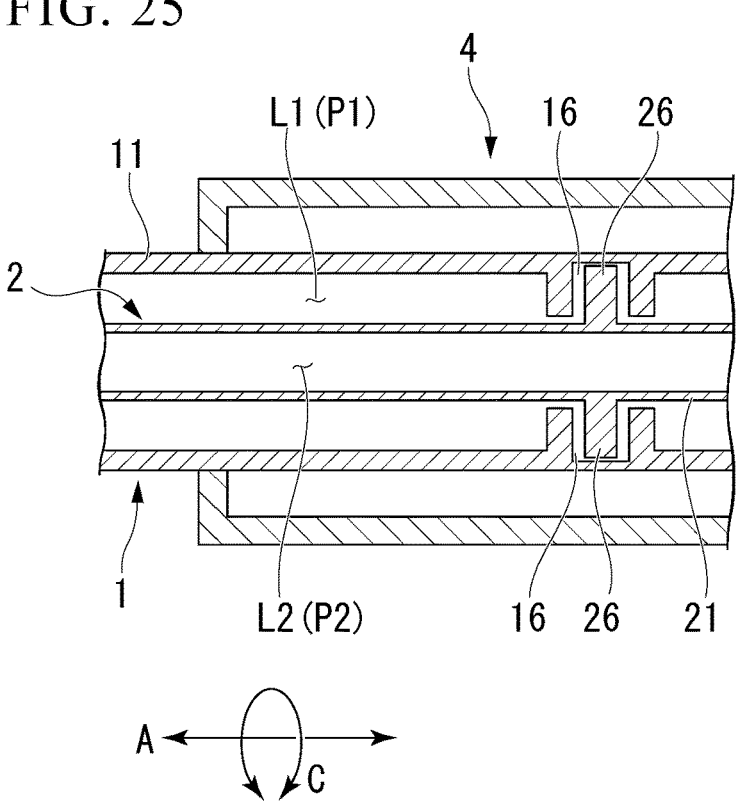
FIG. 25 is a cross-sectional view showing an operation portion of the treatment device.

FIG. 25 is a partial cross-sectional view of the operation portion 4 of the treatment device 100 including the electrode 3G.

The proximal-end portion 21 of the water-supply pipeline 2 has a convex portion 26 protruding outward in the radial direction from the outer peripheral surface. The proximal-end portion 11 of the gas pipeline 1 has a recess 16 on the inner peripheral surface that engages with the convex portion 26. The convex portion 26 and the concave portion 16 are engaged with each other in the axial direction A. Therefore, the gas pipeline 1 and the water-supply pipeline 2 are relatively immovable with each other in the axial direction A.

Another exemplary embodiment will be described with reference to FIG. 26 to FIG. 34. In the following description, the same reference signs will be given to the configurations common to those already described, and duplicate description will be omitted. A treatment device 100B according to the present embodiment has a different configuration of electrodes and the like as compared with the treatment device 100 according to the above embodiment.

Figure 26:
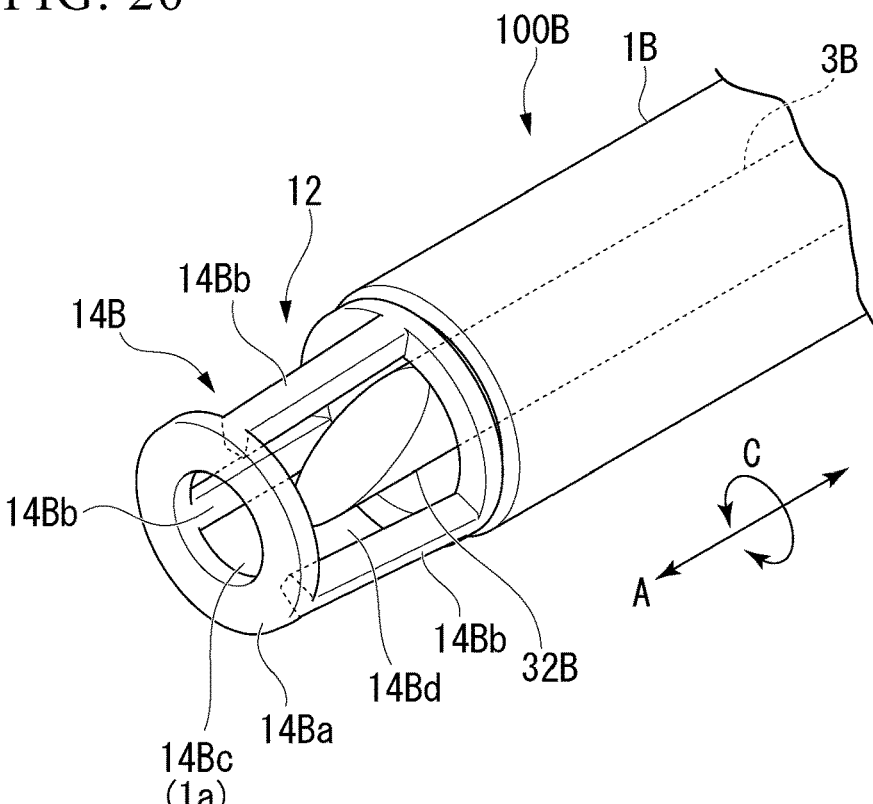
FIG. 26 is a perspective view showing a distal-end portion of a treatment device according to an exemplary embodiment of the present disclosure.
Figure 27:
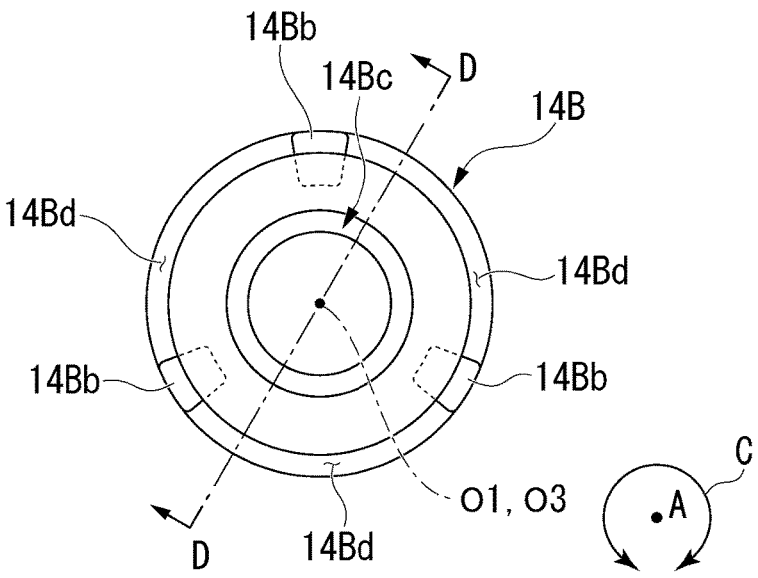
FIG. 27 is a front view showing the distal-end portion of the treatment device.
Figure 28:
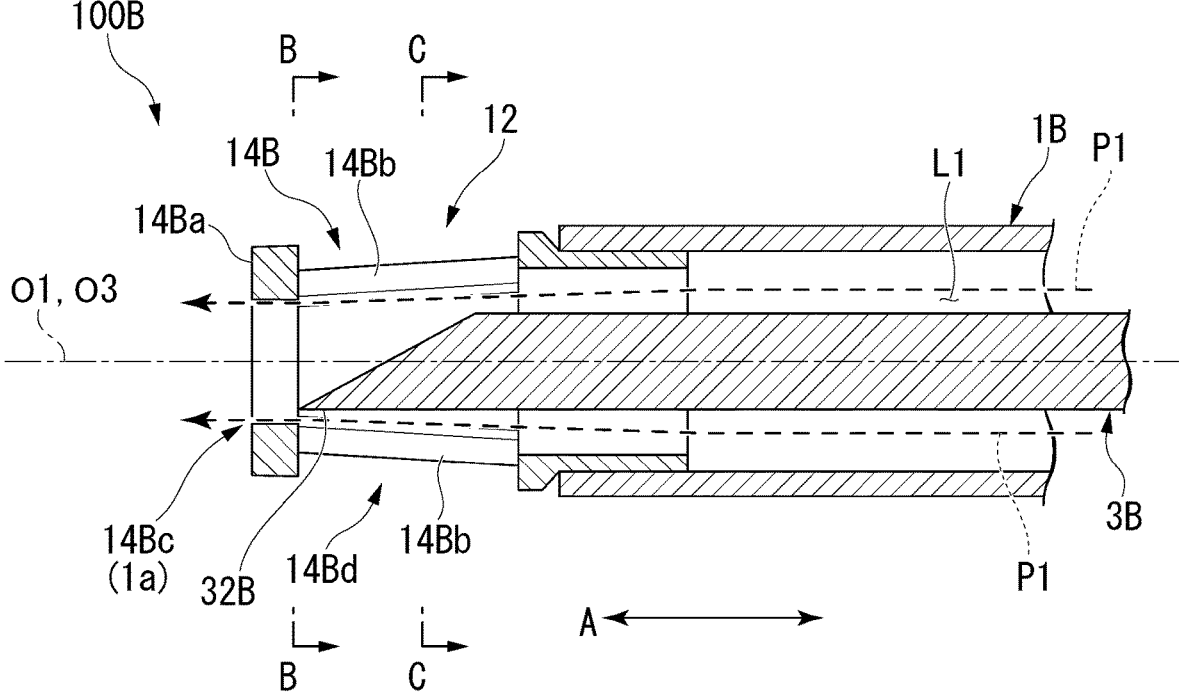
FIG. 28 is a cross-sectional view along a cross section D-D shown in FIG. 27.
Figure 29:
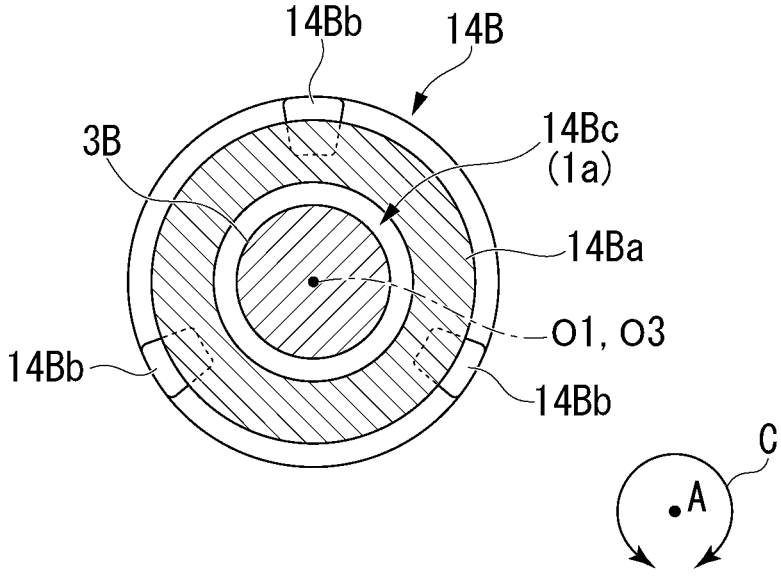
FIG. 29 is a cross-sectional view along a cross section B-B shown in FIG. 28.
Figure 30:
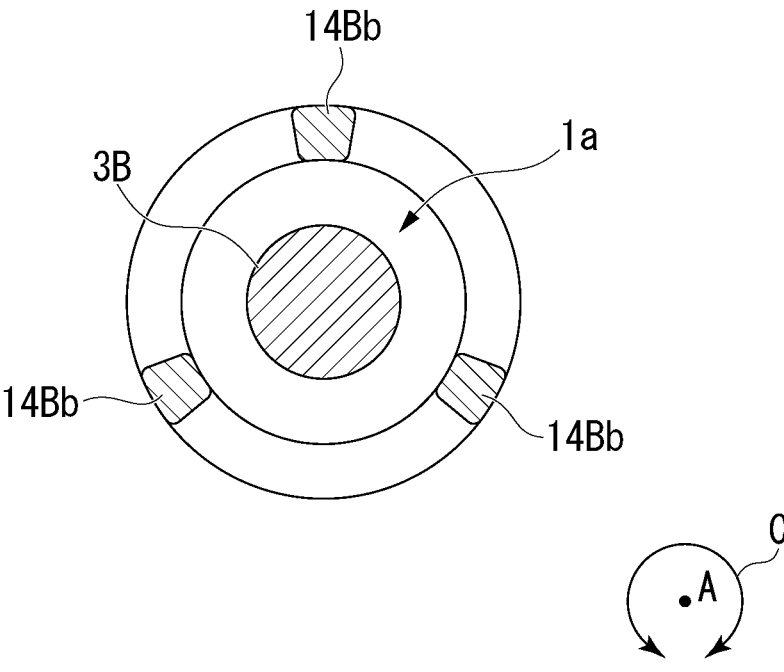
FIG. 30 is a cross-sectional view along a cross section C-C shown in FIG. 28.

FIG. 26 is a perspective view of the distal-end portion of the treatment device 100B. FIG. 27 is a front view of the distal-end portion of the treatment device 100B. FIG. 28 is a cross-sectional view taken along the cross section D-D shown in FIG. 27. FIG. 29 is a cross-sectional view taken along the cross section B-B of FIG. 28. FIG. 30 is a cross-sectional view taken along the cross section C-C of FIG. 28. The cross-sectional views of the distal-end portion of the treatment device shown in this embodiment and the following embodiment are cross-sectional views taken along the cross section D-D shown in FIG. 27.

The treatment device 100B includes a gas pipeline 1B, an electrode 3B, and an operation portion 4B.

As shown in FIG. 26 to FIG. 28, the gas pipeline (first pipeline) 1B is a tubular member having an outer diameter so as to be insertable through the treatment device channel 230 of the endoscope 200. The tubular member is elongated and flexible. The internal space L1 of the gas pipeline 1B is a part of the gas flow path P1 through which inert gas such as the argon gas flows. The gas pipeline 1B is made of a material having electrical insulation such as the PTFE (Poly Tetra Fluoro Ethylene). The proximal-end portion 11 of the gas pipeline 1B is attached to the operation portion 4B.

As shown in FIG. 26 to FIG. 30, the gas pipeline 1B has a distal-end opening 14Bc (first opening 1a) and a side opening 14Bd at the distal-end portion 12. The distal-end opening 14Bc (first opening 1a) and the side opening 14Bd communicate with the internal space L1 of the gas pipeline 1B such that the inert gas can be discharged. The internal space L1 of the gas pipeline 1B extends along the longitudinal axis from the distal-end opening 14Bc to the proximal end of the gas pipeline 1B. The inert gas injected from the gas-supply port 42a flows through the internal space L1 of the gas pipeline 1B and is discharged from the distal-end opening 14Bc (first opening 1a) and the side opening 14Bd of the gas pipeline 1B.

More specifically, the distal-end tip 14B is attached to the distal-end portion 12 of the gas pipeline 1B. As shown in FIG. 26, the distal-end tip 14B has an annular frame 14Ba and three frames 14Bb. The annular frame 14Ba is provided on the distal-end side of the distal-end tip 14B and has a distal-end opening 14Bc (first opening 1a). As shown in FIG. 29 and FIG. 30, the three frames 14Bb are evenly arranged in the circumferential direction C. Three side openings 14Bd are formed between the frames 14Bb. Although the example in which the side openings 14Bd provided on the side of the gas pipeline 1B open in three different directions is described, the embodiment of the openings provided on the side of the gas pipeline 1B is not limited to this example. The openings provided on the side of the gas pipeline 1B may be opened in two different directions.

The electrode 3B is a wire-shaped member and is arranged in the internal space L1 of the gas pipeline 1B. Similar to the above embodiment, the electrode 3B is made of a metal material, has conductivity, and is energizable by a high frequency current. The most proximal end of the proximal-end portion 31 of the electrode 3B is connected to a high frequency power supply 413 that supplies the high frequency current. As shown in FIG. 28, for example, the distal-end portion 32B of the electrode 3B is arranged on the proximal end side of the distal-end opening 14Bc in the axial direction A. More specifically, the distal-end portion 32B of the electrode 3B is arranged in the distal-end tip 14B such that the distal-end portion 32B is not advanceable and retractable in the axial direction A. As shown in FIG. 29, it is preferable that the central axis O2 of the electrode 3B substantially coincides with the central axis O1 of the gas pipeline 1B. Also, preferably, the distal-end opening 14Bc of the distal-end tip 14B is formed on the central axis of the electrode 3B. Furthermore, preferably, the inner diameter of the distal-end opening 14Bc of the distal-end tip 14B is larger than the outer diameter of the electrode 3B.

Figure 31:
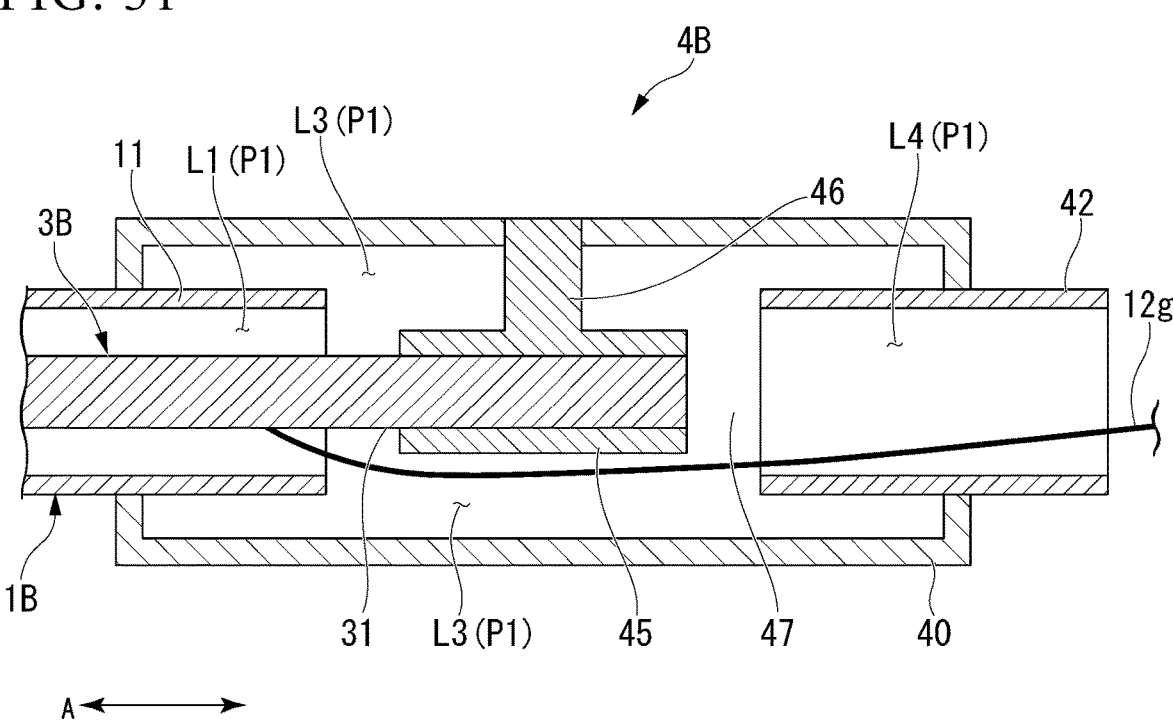
FIG. 31 is a cross-sectional view showing an operation portion of the treatment device.

FIG. 31 is a cross-sectional view showing the operation portion 4B.

The operation portion 4B does not have the slider 43 according to the above embodiment, and the proximal-end portion 11 of the gas pipeline 1B and the proximal-end portion 31 of the electrode 3B are fixed to the operation portion main body 40.

Next, the effects of the treatment device 100B according to the present embodiment will be described. The treatment device 100B, similar to the treatment device 100 according to the above embodiment, can be used in combination with the endoscope 200 for the endoscopic treatment method for the gastroesophageal reflux disease (GERD).

The surgeon specifies the treatment region R as in the above embodiment (treatment region identification step). The surgeon bulges the treatment region R by locally injecting the liquid into the submucosal layer N of the identified treatment region R (local injection step). Similar to that according to the above embodiment, the method of performing the local injection with respect to the treatment region R includes the frontal approach AP1 and the tangential approach AP2.

The surgeon locally injects the liquid into the submucosal layer N of the treatment region R with a well-known local injection needle in the frontal approach AP1, and subsequently locally injects the liquid into the submucosal layer N in the treatment region R in the tangential approach AP2. The sequence of the frontal approach AP1 and the tangential approach AP2 may be interchanged, and the local injection in the frontal approach AP1 may be performed after the local injection in the tangential approach AP2 is performed.

Next, the surgeon cauterizes the treatment region R (cauterization step). At this time, only the cauterization is performed without resecting the mucous membrane. The degree of the cauterization is such that the mucosa basal layer M is damaged as the same according to the above embodiment.

Figure 32:
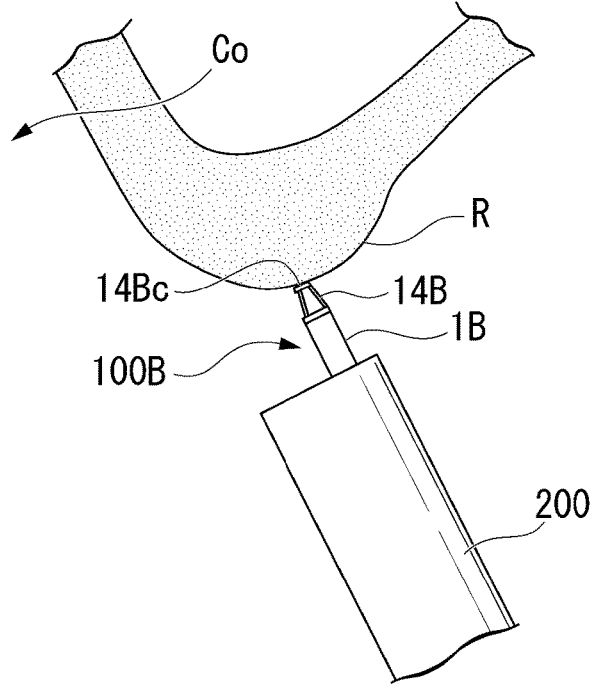
FIG. 32 is a view showing the treatment device that is deployed at a position to cauterize the treatment region by a frontal approach.

FIG. 32 is an enlarged view showing the region R1 shown in FIG. 8, and FIG. 32 is a view showing the treatment device 100B arranged at a position where the treatment region R is cauterized by the frontal approach AP1. In the frontal approach AP1, the surgeon arranges the treatment device 100B such that the distal-end opening 14Bc faces the treatment region R by moving the treatment device 100B or the distal-end portion 201 of the endoscope 200.

Figure 33:
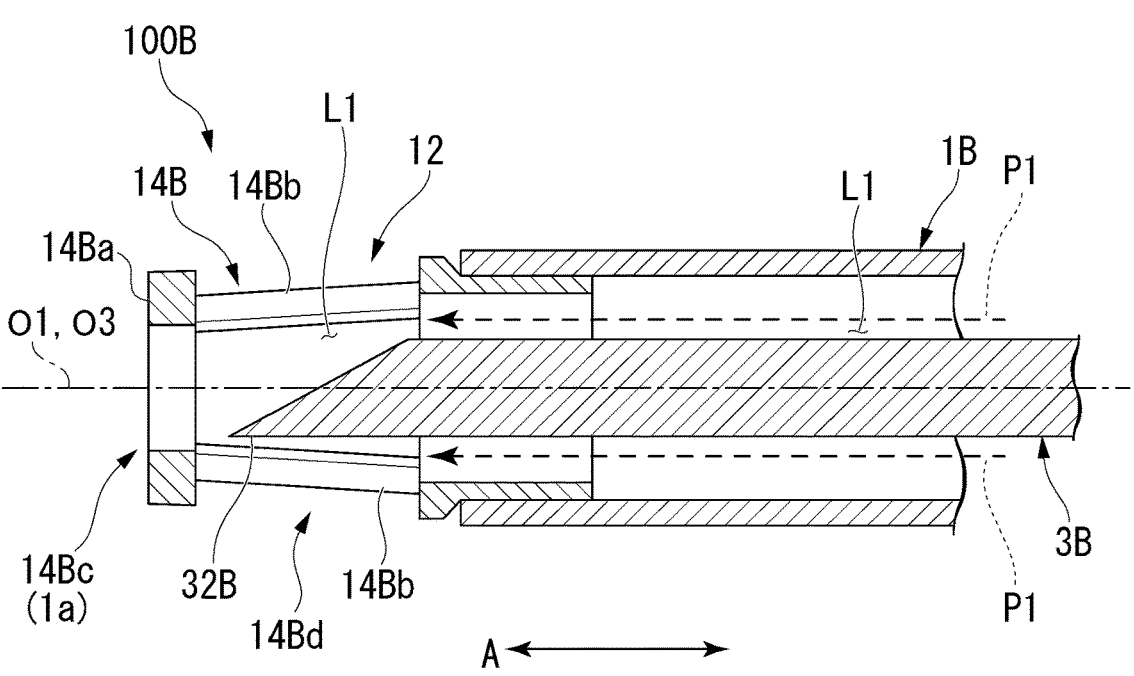
FIG. 33 is a cross-sectional view showing the distal-end portion of the treatment device when cauterizing the treatment region.

FIG. 33 is a cross-sectional view of the tip of the treatment device 100B when cauterizing the treatment region R.

The surgeon supplies the inert gas to the gas supply port 42a. As shown in FIG. 33, the supplied inert gas is discharged from the distal-end opening 14Bc (first opening 1a) and the side opening 14Bd via the gas flow path P1. The surgeon cauterizes the treatment region R while supplying the inert gas to the vicinity of the treatment region R and supplying the high-frequency current to the electrode 3B. At that time, since the distal-end portion 32B of the electrode 3B is located inside the distal-end tip 14B, the electrode 3B and the treatment region R do not come into contact with each other.

By discharging the high-frequency current in the inert gas, the inert gas is ionized and becomes plasma P. The plasma P promotes stable maintenance of the discharge from the distal-end portion 32B of the electrode 3B toward the treatment region R via the distal-end opening 14Bc or the side opening 14Bd.

Figure 34:
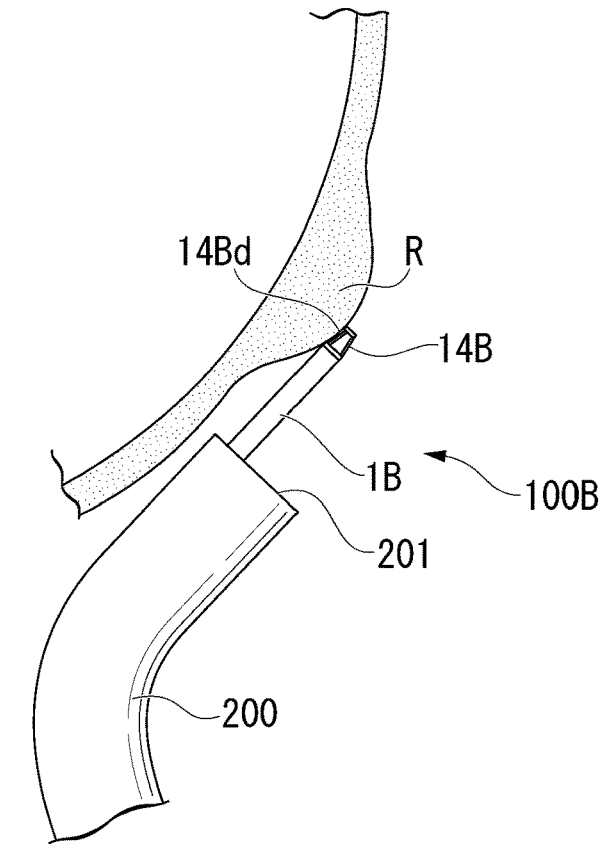
FIG. 34 is a view showing the treatment device that is deployed at a position to cauterize the treatment region by a tangential approach.

FIG. 34 is an enlarged view showing the R2 region shown in FIG. 8 and FIG. 34 is a view showing the treatment device 100B arranged at the position where the treatment region R is cauterized by the tangential approach AP2. After cauterizing the treatment region R in the frontal approach AP1, the treatment region R is subsequently cauterized in the tangential approach AP2. In the tangential approach AP2, the surgeon arranges the treatment device 100B such that the side opening 14Bd of the gas pipeline 1B faces the treatment region R by operating the treatment device 100B or the endoscope 200.

In a state in which the side opening 14Bd of the gas pipeline 1B approaches the treatment region R, the inert gas is discharged from the side opening 14Bd. Also, the surgeon cauterizes the treatment region R while supplying the inert gas to the vicinity of the treatment region R and supplying the high frequency current to the electrode 3B. At that time, since the distal-end portion 32B of the electrode 3B is located inside the distal-end tip 14B, the electrode 3B and the treatment region R do not come into contact with each other.

The sequence of the frontal approach AP1 and the tangential approach AP2 may be interchanged, and the cauterization in the frontal approach AP1 may be performed after the cauterization in the tangential approach AP2 is performed.

At the time of cauterizing the treatment region R, the distal-end portion 32B of the electrode 3B is arranged in the distal-end tip 14B. Therefore, scorching due to the contact between the distal-end portion 32B of the electrode 3B and the tissue during cauterization is difficult to occur.

According to the treatment device 100B disclosed in the present embodiment, since the range that can be cauterized at once is wider than that by the treatment device such as the high-frequency knife or the like, it is possible to quickly cauterize a wide treatment range R. In addition, in a case in which the distal-end opening 14Bc of the distal-end tip 14B is formed on the central axis of the electrode 3B, the treatment region R can be efficiently cauterized by the plasma P. Also, when the inner diameter of the distal-end opening 14Bc of the distal-end tip 14B is larger than the outer diameter of the electrode 3B, the cauterization can be performed more efficiently.

Since the mucosa basal layer M of is damaged by the cauterization, the gastric mucosa of the treatment region R is subsequently regenerated through the process of scar formation. During the mucosal regeneration, the gastric mucosa surrounding the treatment region R is attracted toward the treatment region R by the contractile action of the tissue surrounding the treatment region R in the process of the scar formation when the damaged mucosa heals. By utilizing this effect, the symptom of GERD is improved by forming an incomplete stenosis in the cardia Co to prevent the reflux symptom.

In a case of cauterizing the gastroesophageal junction around the cardia Co, it is necessary to significantly bend the distal-end portion 201 of the endoscope 200, as shown in FIG. 7. Therefore, it is often difficult to make the first opening 1a of the treatment device 100B to face the treatment region R. Since the treatment device 100B has the side opening 14Bd formed on the lateral side thereof, it is possible to perform the cauterization of the treatment region R that is located at the lateral side by discharging the inert gas from the side opening 14Bd and discharging the high-frequency current in the inert gas.

Although the present embodiment has been described in detail with reference to the drawings, the specific configuration is not limited to this embodiment, and includes design changes and the like within a range that does not deviate from the scope of the present disclosure. In addition, the components shown in the above-described embodiments and modification examples can be appropriately combined and configured.

Another exemplary embodiment of the present disclosure will be described with reference to the drawings. In the following description, the same reference signs will be given to the configurations common to those already described, and duplicate description will be omitted. The treatment device 100C according to the present embodiment has a different electrode configuration as compared with the treatment device 100B according to the above embodiment described with respect to FIGS. 26-34.

Figure 35:
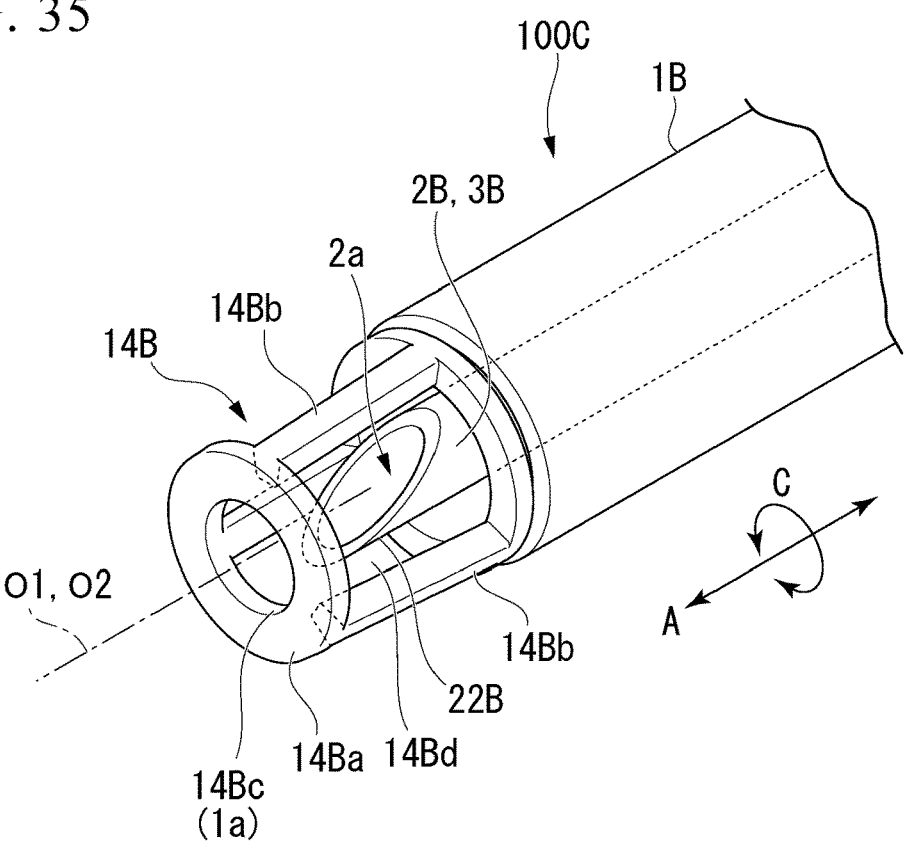
FIG. 35 is a view showing a distal-end portion of a treatment device according to an exemplary embodiment.
Figure 36:
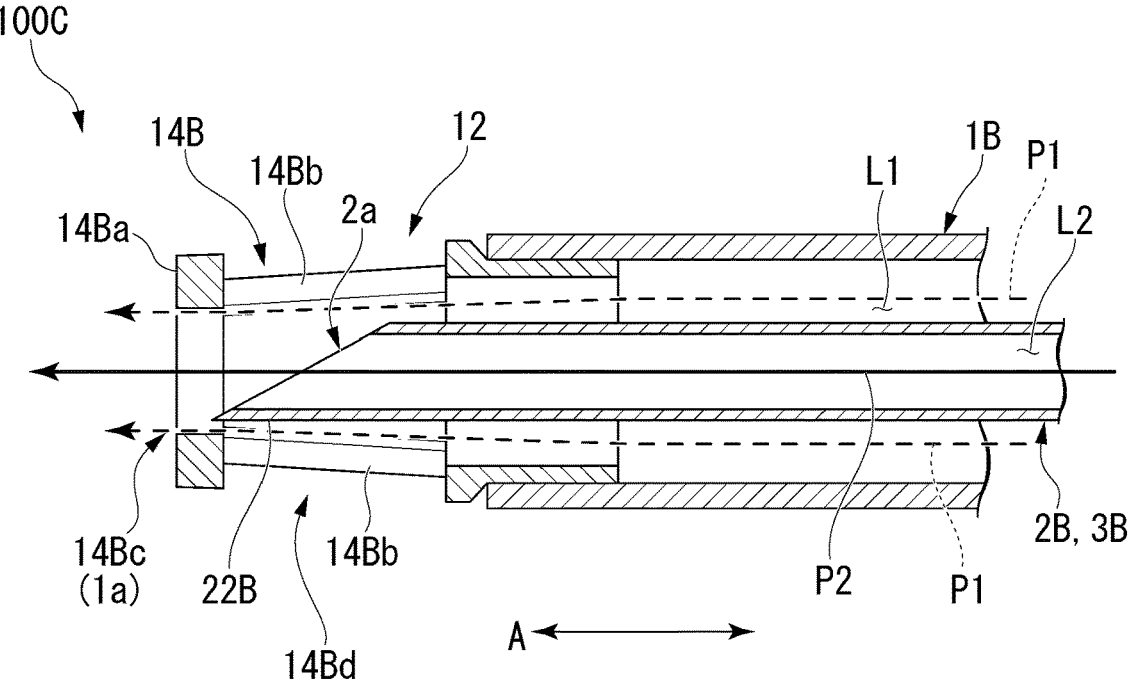
FIG. 36 is a cross-sectional view showing the distal-end portion of the treatment device.

FIG. 35 is a perspective view showing the distal-end portion of the treatment device 100C in which the electrode 3B includes the water-supply pipeline (second pipeline) 2B. FIG. 36 is a cross-sectional view showing the distal-end portion of the treatment device 100C. As shown in FIG. 35 and FIG. 36, the electrode 3B may include a water-supply pipeline (second pipeline) 2B.

The water-supply pipeline 2B has an outer diameter smaller than the inner diameter of the gas pipeline 1B. The distal-end portion 32B of the water-supply pipeline 2B is cut diagonally with respect to the axial direction A to form a needle shape, and functions as a "puncture needle".

The proximal-end portion 31 of the water-supply pipeline 2B is attached to the operation portion 4B. By operating the operation portion 4B, it is possible to advance and retract the water-supply pipeline 2B in the axial direction A of the treatment device 100C. The distal-end portion 32B of the water-supply pipeline 2B is freely advanceable and retractable between the first position at the distal side of the gas pipeline 1B and the second position in the internal space L1 of the gas pipeline 1B. That is, the distal-end portion 32B of the water-supply pipeline 2B can be moved to the first position by projecting from the distal-end opening 14Bc of the gas pipeline 1B, and the water-supply pipeline 2B can be moved to the second position by drawing the distal-end portion 32B of the water-supply pipeline 2B into the internal space L1 of the gas pipeline 1B.

Specifically, the operation portion 4B has a slider 43B similar to the slider 43 according to the above embodiment described with respect to FIGS. 1-21. The proximal-end portion 11 of the gas pipeline 1B is fixed to the operation portion main body 40 of the operation portion 4B. On the other hand, the water-supply pipeline 2B is attached to the slider 43B of the operation portion 4B so as to be freely advanceable and retractable in the axial direction A. Therefore, by advancing and retracting the slider 43B with respect to the operation portion main body 40, the water-supply pipeline 2B also advances and retracts with respect to the gas pipeline 1B.

Figure 37:
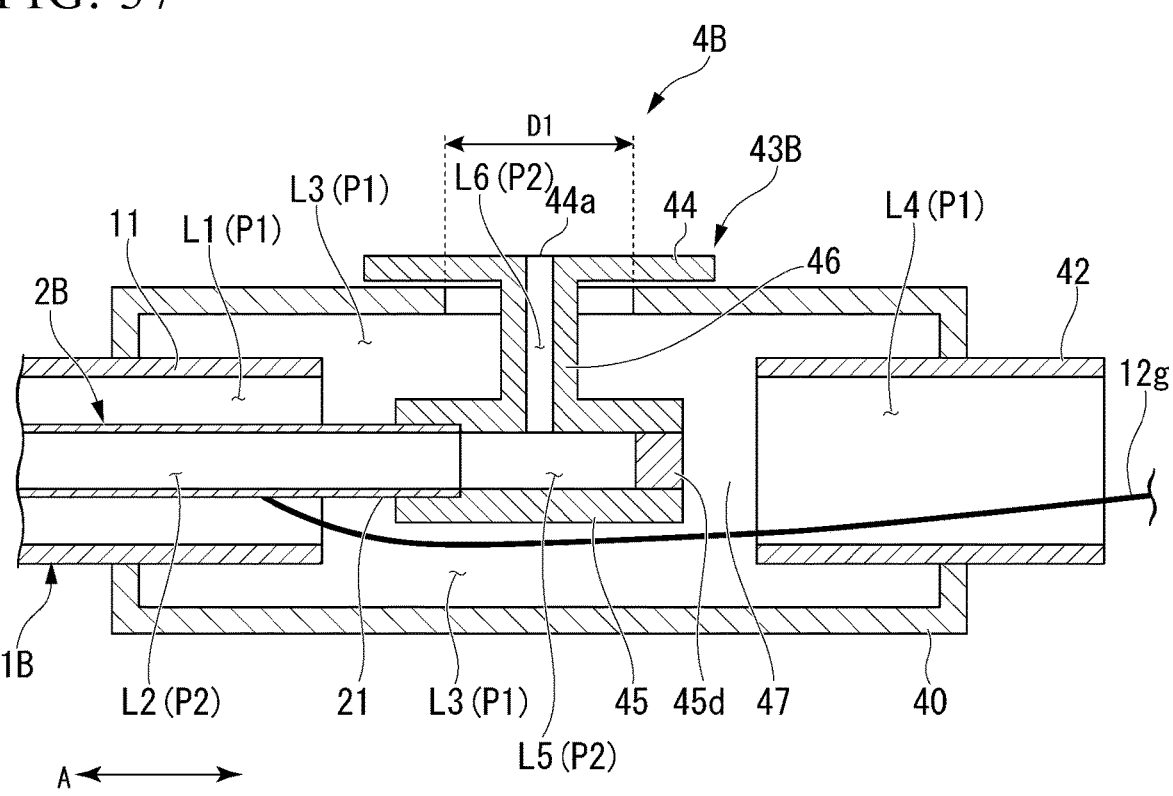
FIG. 37 is a cross-sectional view showing an operation portion of the treatment device.

FIG. 37 is a cross-sectional view of the operation portion 4B to which the gas pipeline 1B and the water-supply pipeline 2B are connected.

The internal space L5 of the water-supply pipeline 45 communicates with the internal space L2 and the internal space L6. The boundary between the internal space L5 and the internal space L3 is sealed by the sealing member 45d. The proximal-end portion 21 of the water-supply pipeline 2B is connected to the high frequency power supply 413 that supplies a high frequency current via a wire 12g.

The water-supply pipeline 2B is a tubular member, and is inserted into the internal space L1 of the gas pipeline 1B so as to be relatively movable. The internal space L2 of the water-supply pipeline 2B is a part of the water flow path P2 through which the liquid such as the physiological saline or the like flows.

The water-supply pipeline 2B has a second opening 2a at the distal-end portion 22B. The liquid supplied to the liquid supply port 44a flows through the internal space L6 of the support column portion 46, the internal space L5 of the water-supply pipeline 45, and the internal space L2 of the water-supply pipeline 2 to be discharged from the second opening 2a of the distal-end portion 22B of the water-supply pipeline 2B.

Figure 38:
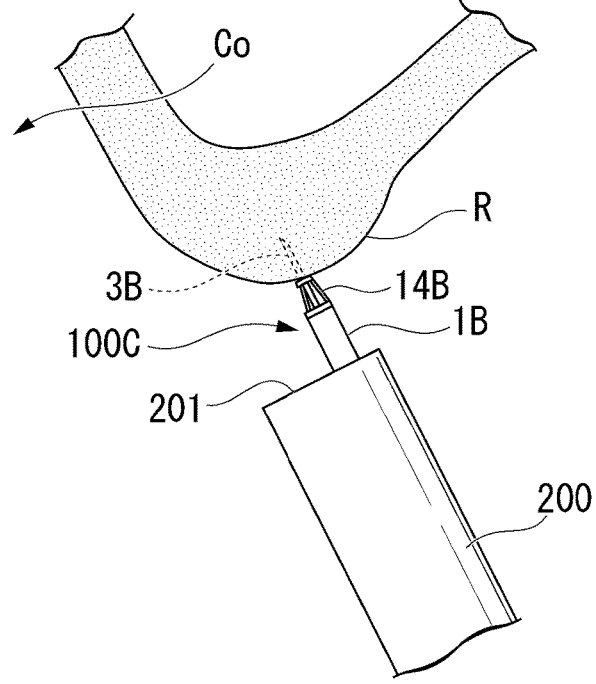
FIG. 38 is a view showing the treatment device that is deployed at a position to perform the local injection to the treatment region by the frontal approach.

FIG. 38 is a view showing the treatment device 100C arranged at a position for performing the local injection with respect to the treatment region R by the frontal approach AP1.

In the frontal approach AP1, the surgeon advances the water-supply pipeline 2B relative to the gas pipeline 1B by advancing the slider 43B with respect to the operation portion main body 40. Then, the distal-end portion 32B of the water-supply pipeline 2B is projected from the first opening 1a of the gas pipeline 1B (first state). By this operation, the distal-end portion 32B of the water-supply pipeline 2B moves to the first position. The surgeon can easily position the distal-end portion 32B of the water-supply pipeline 2B to the first position by moving the slider 43B to the most distal side of the advance-retract range D1. As shown in FIG. 38, the surgeon punctures the distal-end portion 32B of the water-supply pipeline 2B protruding from the distal-end opening 14Bc (first opening 1a) into the treatment region R. The surgeon advances the water-supply pipeline 2B until the distal-end portion 32B of the water-supply pipeline 2B penetrates the mucosal layer L and reaches the submucosal layer N. The surgeon supplies the liquid to the liquid-supply port 44a in a state where the distal-end portion 32B of the water-supply pipeline 2B penetrates the mucosal layer L and reaches the submucosal layer N. The supplied liquid is supplied from the second opening 2a of the distal-end portion 22B of the water-supply pipeline 2B via the water supply flow path P2, and is locally injected into the submucosal layer N. The treatment region R to which the liquid is locally injected bulges.

Figure 39:
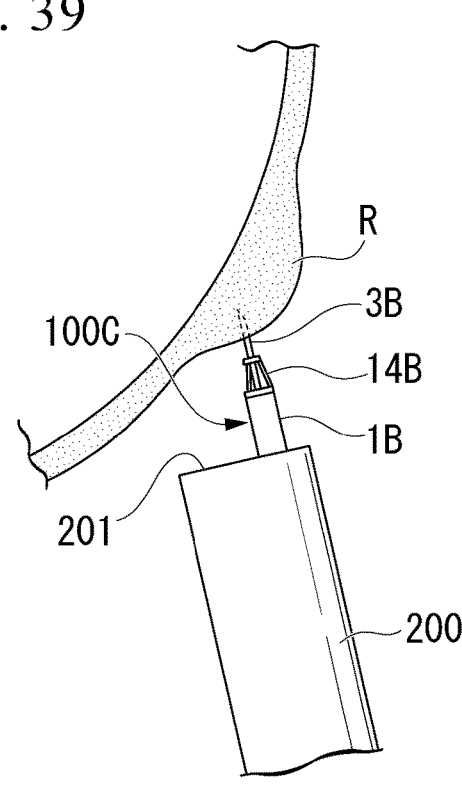
FIG. 39 is a view showing the treatment device that is deployed at a position to perform the local injection to the treatment region by the tangential approach.

FIG. 39 is a view showing the treatment device 100C arranged at a position where the treatment region R is locally injected by the tangential approach AP2.

After the local injection with respect to the treatment region R by the frontal approach AP1 is performed, sequentially in the tangential approach AP2, as shown in FIG. 39, the surgeon punctures the distal-end portion 32B of the water-supply pipeline 2B protruding from the distal-end opening 14Bc (first opening 1a) into the treatment region R. The surgeon advances the water-supply pipeline 2B until the distal-end portion 32B of the water-supply pipeline 2B penetrates the mucosal layer L and reaches the submucosal layer N.

Similar to the frontal approach AP1, the surgeon supplies the liquid to the liquid-supply port 44a. The supplied liquid is supplied from the second opening 2a of the distal-end portion 22B of the water-supply pipeline 2B via the water supply flow path P2, and is locally injected into the submucosal layer N. The treatment region R to which the liquid is locally injected bulges.

With regard to the frontal approach AP1 and the tangential approach AP2, the surgeon retracts the distal-end portion 22B of the water-supply pipeline 2B with respect to the gas pipeline 1B by retracting the slider 43B with respect to the operating unit body 40. As a result, the distal-end portion 22B of the water-supply pipeline 2B is removed from the mucosal layer L and the submucosal layer N.

Subsequently, the surgeon further retracts the slider 43B with respect to the operation portion main body 40 so as to retract the water-supply pipeline 2 relative to the gas pipeline 1. Then, the distal-end portion 32B of the water-supply pipeline 2B is drawn into the internal space L1 of the gas pipe line 1B, more preferably retracted into the distal-end tip 14 (second state). By this operation, the distal-end portion 32B of the water-supply pipeline 2B moves to the second position. By moving the slider 43B to the most proximal end of the advance-retract range D1, the surgeon can easily position the distal-end portion 32B of the water-supply pipeline 2B to the second position.

Next, the surgeon starts the cauterization step with respect to the treatment region R without removing the treatment device 100C from the endoscope 200. After the cauterization step, the procedure proceeds in the same steps as that in the above embodiment described with respect to FIGS. 26-34.

In a case of using the water-supply pipeline 2B, it is possible for the surgeon to repeat the local injection and the cauterization treatment without removing the treatment device 100C from the treatment device channel 230 and replacing the treatment device.

Figure 40:
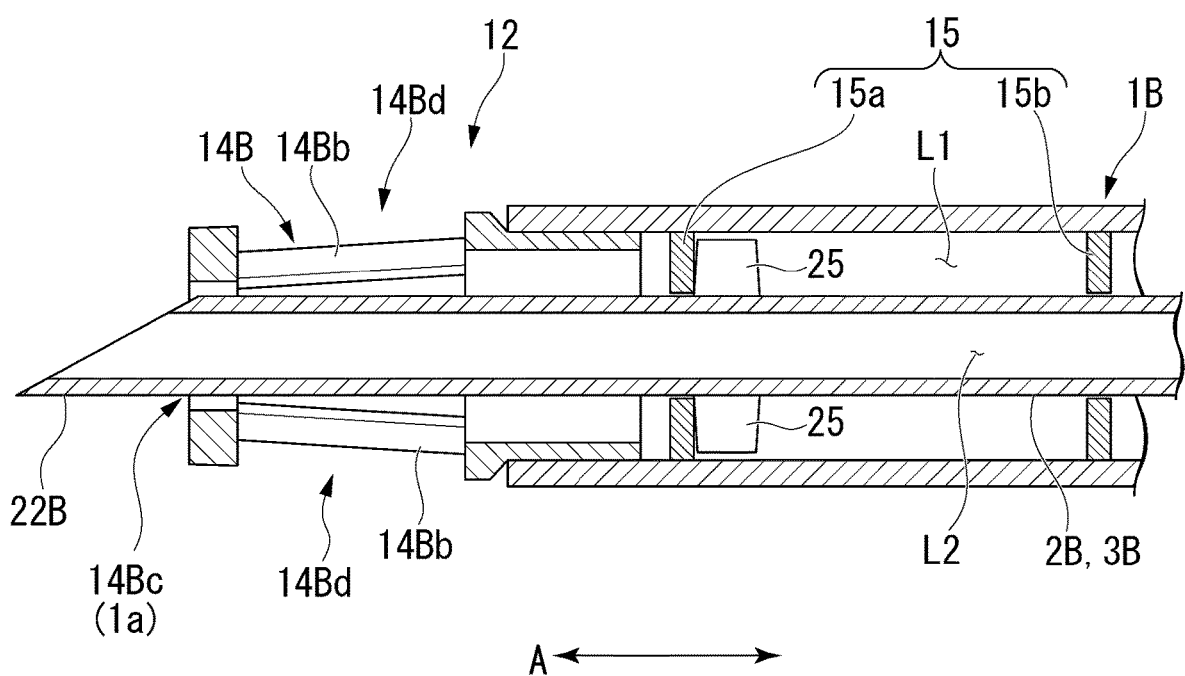
FIG. 40 is a cross-sectional view showing a distal-end portion of a modification example of the treatment device.

FIG. 40 is a cross-sectional view (cross section D-D) of the distal-end portion of the modification example of the treatment device 100C.

The water-supply pipeline 2B (electrode 3B) may further include an engaging member 25. The engaging member 25 is a member provided on the outer periphery of the water-supply pipeline 2B, and protrudes in the radial direction from the outer periphery of the water-supply pipeline 2B. The gas pipeline (first pipeline) 1B may further have a stopper 15. The stopper 15 is provided to project from the inner peripheral surface of the gas pipeline 1B in the internal space L1 of the gas pipeline 1B so as to regulate the advancement/retraction range of the electrode 3B.

The stopper 15 has a first stopper 15a and a second stopper 15b. The first stopper 15a and the second stopper 15b are located apart from each other in the axial direction A. Specifically, the second stopper 15b is located closer to the proximal end side of the gas pipeline 1B than the first stopper 15a.

Figure 41:
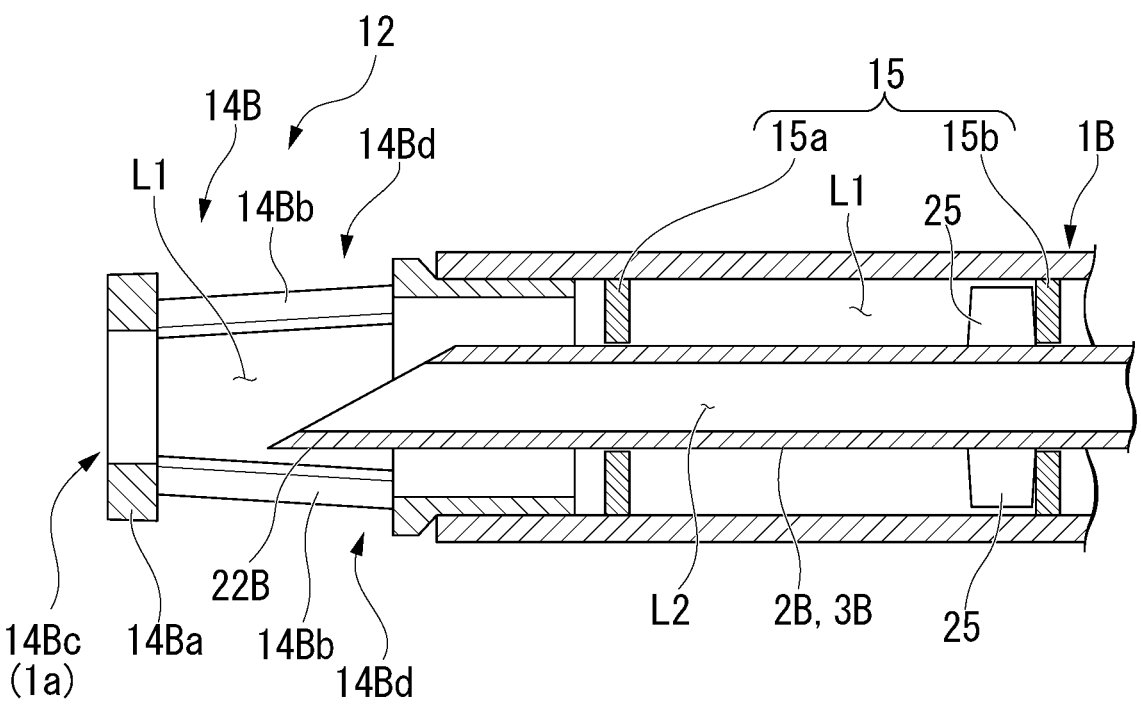
FIG. 41 is a cross-sectional view showing the distal-end portion of the modification example of the treatment device whose retraction movement is restricted.

FIG. 41 is a cross-sectional view showing the cross section D-D according to the modification example of the treatment device 100C in which the retraction movement of the water-supply pipeline 2B is regulated.

As shown in FIG. 40, the advancement of the water-supply pipeline 2B is regulated by the engaging member 25 engaging with the first stopper 15a. As shown in FIG. 41, the retraction movement of the water-supply pipeline 2B is regulated by the engaging member 25 engaging with the second stopper 15b.

The engaging member 25 is fixed to the electrode 3B at a position between the first stopper 15a and the second stopper 15b. The first stopper 15a is a member that regulates the advancement of the water-supply pipeline 2B by the engaging member 25 abutting against the proximal end of the first stopper 15a. The second stopper 15b is a member that regulates the retraction movement of the water-supply pipeline 2B by the engaging member 25 abutting against the distal end of the second stopper 15b. In a case in which the engaging member 25 abuts against the proximal end of the first stopper 15a, as shown in FIG. 40, the distal-end of the water-supply pipeline 2B protrudes from the distal-end opening 14Bc. On the other hand, in the case in which the engaging member 25 abuts against the distal end of the second stopper 15b, as shown in FIG. 41, in the longitudinal axis direction of the gas pipeline 1B, the position of the distal end of the water-supply pipeline 2B is determined between the distal end and the proximal end of the side opening.

A length of an advance-retract regulation range D2 (distance between the first stopper 15a and the second stopper 15b) of the water-supply pipeline 2B regulated by the stopper 15 is equal to or less than the length of the advance-retract range D1 of the slider 43B.

Therefore, regardless of the curved shape of the gas pipeline 1B, the engaging member 25 engages with the first stopper 15a to regulate the advancement of the water-supply pipeline 2B before the slider 43B moves to the most proximal end of the advance-retract range D1. It is easier for the surgeon to position the distal-end portion 32B of the water-supply pipeline 2B to the first position by abutting the engaging member 25 on the proximal end of the first stopper 15a.

Figure 42:
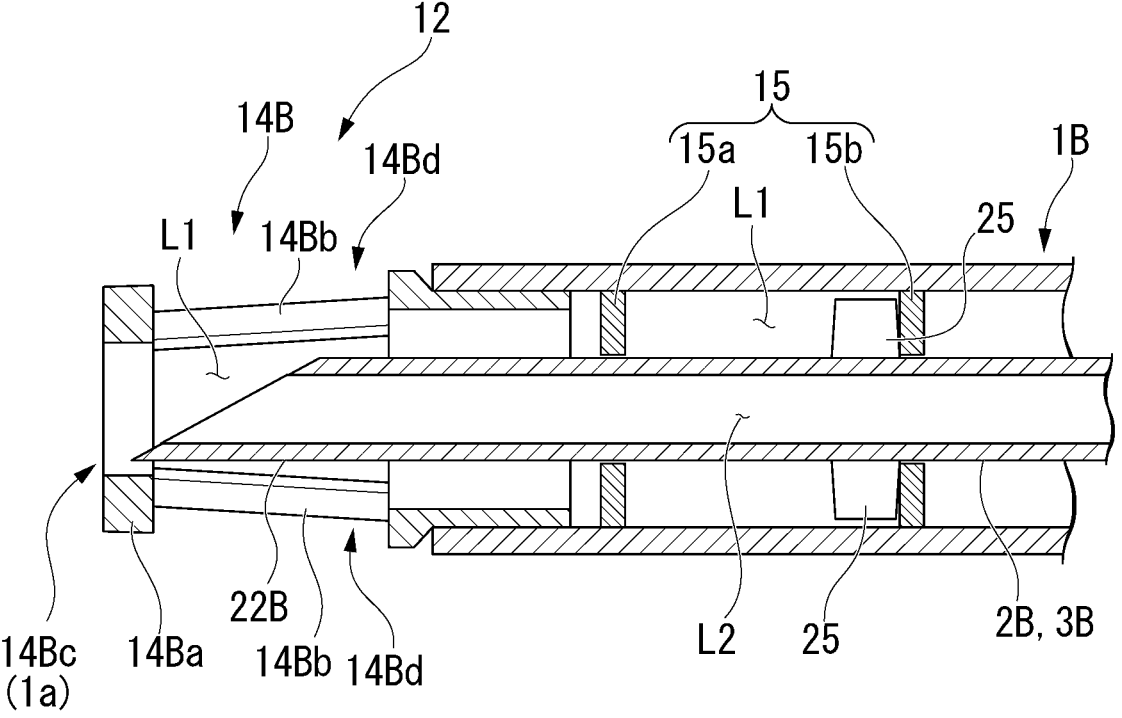
FIG. 42 is a cross-sectional view showing a distal-end portion of a modification example of the treatment device.

FIG. 42 is a cross-sectional view showing a distal-end portion of a modification example of the treatment device 100C.

As shown in FIG. 42, the most distal end of the distal-end portion 32B positioned at the second position may be located between the distal-end opening 14Bc and the distal end of the side opening 14Bd in the axial direction A. The treatment device 100C is configured to discharge the high-frequency current in the inert gas discharged from the side opening 14Bd. The treatment device 100C can suppress the deterioration of the most distal end of the distal-end portion 32B due to the electric discharge by regulating the exposure of the most distal end of the distal-end portion 22B.

Although the present embodiment has been described in detail with reference to the drawings, the specific configuration is not limited to this embodiment, and includes design changes and the like within a range that does not deviate from the scope of the present invention. In addition, the components shown in the above-described embodiments and modification examples can be appropriately combined and configured.

Figure 43:
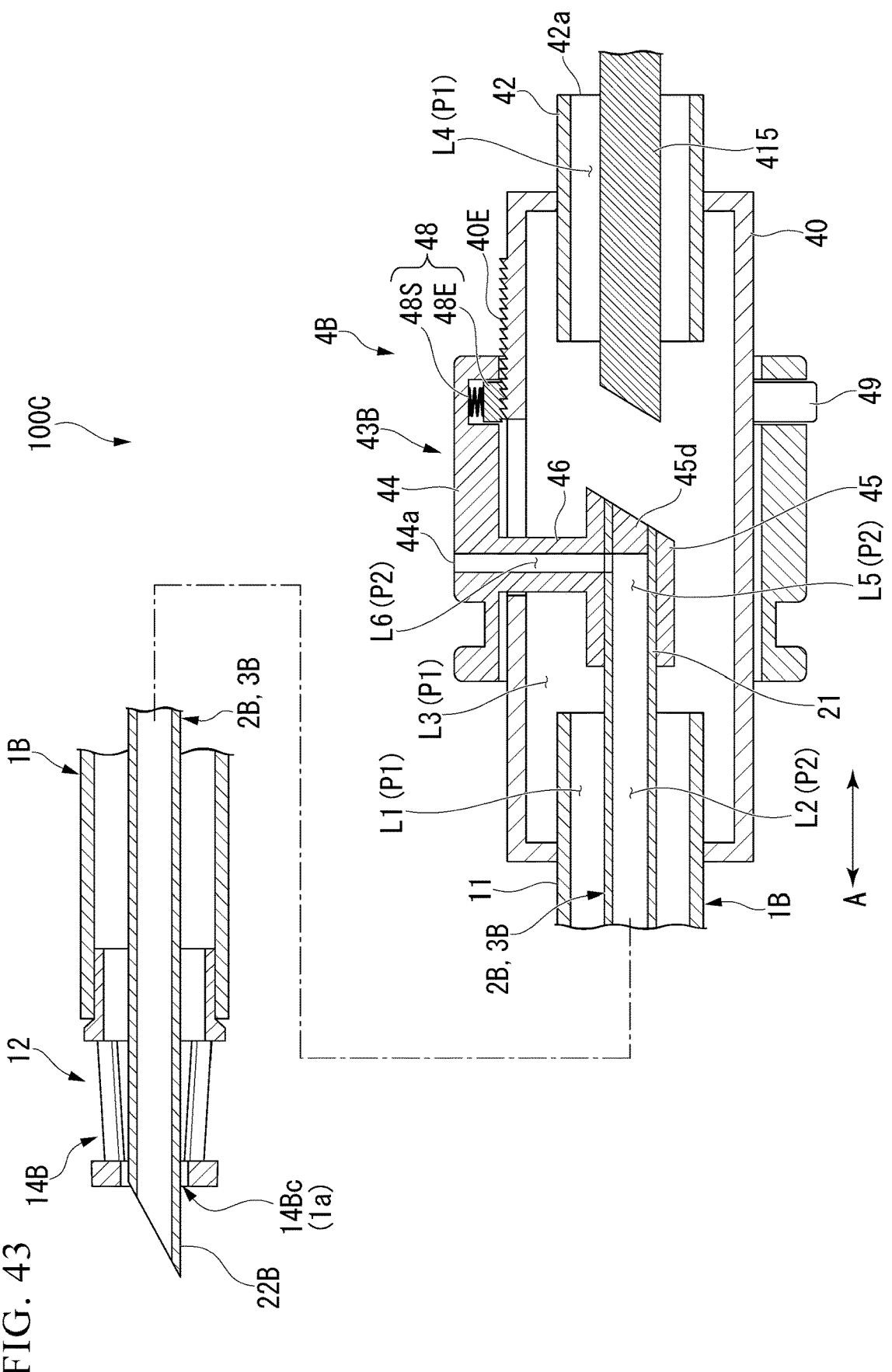
FIG. 43 is a cross-sectional view showing the treatment device in which a slider in the treatment device according to the modification example of the treatment device is positioned at the distal end side.
Figure 44:
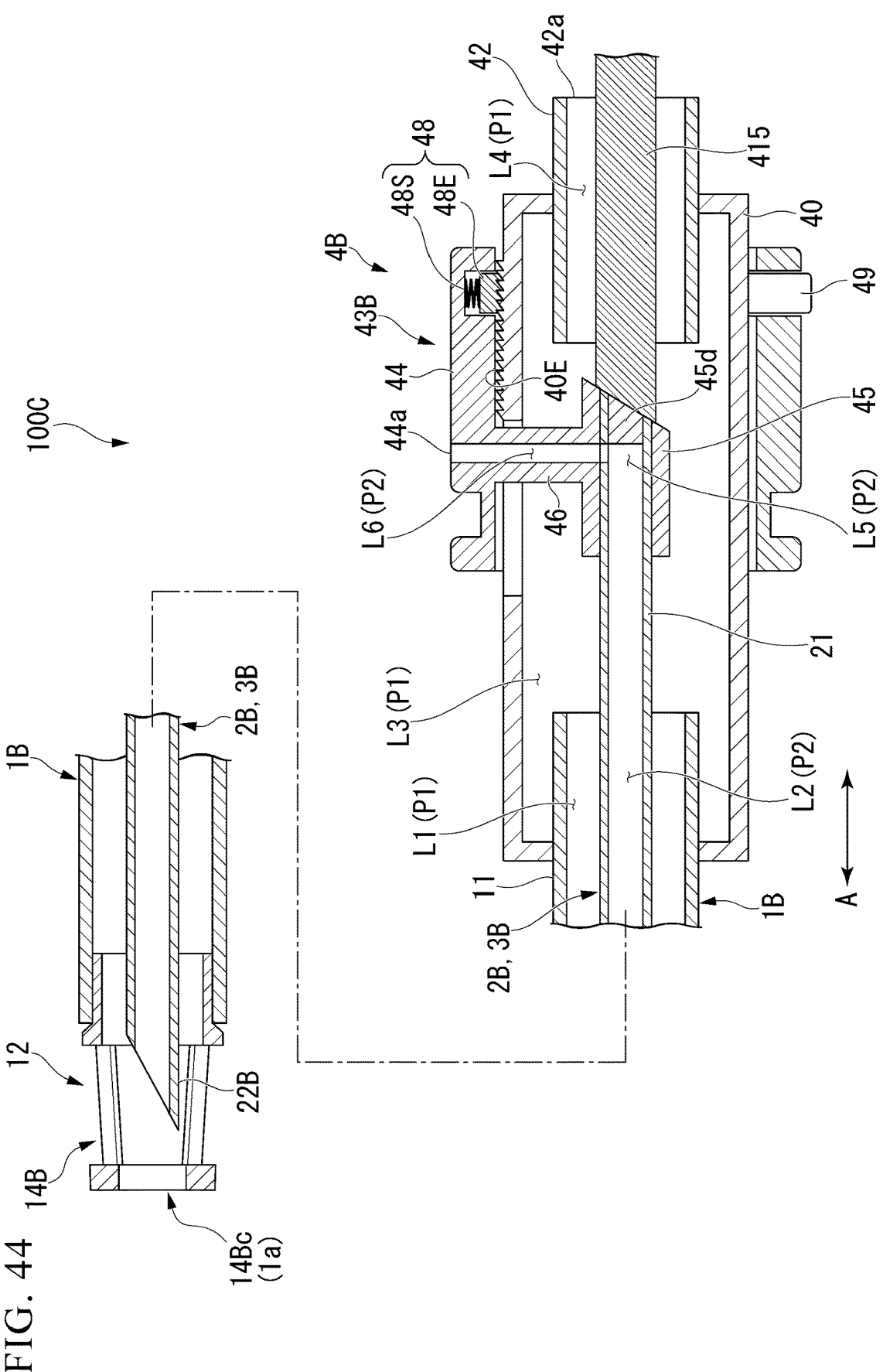
FIG. 44 is a cross-sectional view showing the treatment device in which the slider is positioned at the most proximal end.

FIG. 43 and FIG. 44 show a modification example of the treatment device 100C. As shown in FIG. 43, the slider 43B may have a fixing mechanism 48 and a release button 49.

The slider 43B is attached to the operation portion main body 40 so as to freely advanceable and retractable in the axial direction A. The slider 43B is fixed to the proximal-end portion 31 of the water-supply pipeline 2B. It is possible for the surgeon to advance and retract the water-supply pipeline 2B along the axial direction A with respect to the gas pipeline 1B by advancing and retracting the slider 43B in the axial direction A.

The fixing mechanism 48 is a ratchet mechanism provided on the slider 43B, and has a spring 48S and an engaging portion (claw) 48E.

FIG. 44 is a cross-sectional view showing the treatment device 100C in which the slider 43B is positioned at the most proximal end.

When the slider 43B retracts, the engaging portion 48E of the fixing mechanism 48 engages with the engaged portion (ratchet tooth) 40E provided on the operation portion main body 40 by the restoring force of the spring 48S. In a case in which the engaging portion 48E and the engaged portion 40E are engaged with each other, the slider 43B cannot advance with respect to the operation portion main body 40. On the other hand, even in the case in which the engaging portion 48E and the engaged portion 40E are engaged with each other, the slider 43B can retract with respect to the operation portion main body 40.

The release button 49 is a button configured to release the engagement between the engaging portion 48E and the engaged portion 40E by being pressed. In a case in which the surgeon presses the release button 49, it is possible for the surgeon to advance the slider 43B with respect to the operation portion main body 40. That is, when the release button 49 is pressed, the engagement (hooking) between the engaging portion 48E and the engaged portion 40E is released such that the slider 43B is advanceable along the axial direction A of the operation portion main body 40 with respect to the operation portion main body 40.

The proximal-end portion of the gas pipeline 1B is fixed to the operation portion main body 40. The proximal-end portion 31 of the water-supply pipeline 2B that functions as the electrode 3B is attached to the slider 43B and is freely advanceable and retractable with respect to the operation portion main body 40. Therefore, as shown in FIG. 44, when the slider 43B is retracted with respect to the operation portion main body 40, the proximal-end portion 31 of the water-supply pipeline 2B is also retracted in the operation portion main body 40. Also, when the slider 43B is advanced with respect to the operation portion main body 40, the proximal-end portion 31 of the water-supply pipeline 2B is also advanced in the operation portion main body 40. On the other hand, the distal-end portion of the electrode (second electrode) 415 is fixed to the operation portion main body 40 by a well-known means in a state of being inserted inside the operation portion main body 40. The proximal-end portion of the electrode 415 has a plug that can be electrically connected to the high frequency power supply 413 that generates a high frequency current, and the plug is connected to the high frequency power supply 413. That is, the proximal-end portion 31 of the water-supply pipeline 2B (electrode 3B) is configured to be electrically switched between contact and non-contact (separation) with the distal-end portion of the electrode 415 in response to the advancement and retraction of the slider 43B with respect to the operation portion main body 40. The proximal-end portion 31 of the water-supply pipeline 2B and the distal-end end portion of the electrode 415 do not necessarily have to be electrically contact inside the operation portion main body 40, and the distal-end portion of the electrode 415 only has to be fixed to the operation portion main body 40 so as to adopt the configuration that the electrically contact and non-contact can be switched at any position outside the operation portion main body 40.

As shown in FIG. 44, when the slider 43B is retracted to the most proximal end, the distal-end portion 32B of the water-supply pipeline 2B is arranged at the second position (internal space L1 of the gas pipeline 1B). At this time, the proximal-end portion 31 of the water-supply pipeline 2B comes into contact with the distal-end portion of the electrode (second electrode) 415.

As a result, the state in which the high frequency current is supplied to the electrode 3B is realized. At this time, since the engaging portion 48E and the engaged portion 40E are engaged with each other, the slider 43B cannot advance with respect to the operation portion main body 40. Therefore, it is possible to prevent the distal-end portion 32B of the water-supply pipeline 2B that functions as the electrode 3B from advancing from the second position to the first position (at the distal side of the gas pipeline 1B) to come into contact with the tissues which is contrary to the intention of the surgeon.

Also, as shown in FIG. 43, when the slider 43B is advanced to the most distal end, the distal-end portion 32B of the water-supply pipeline 2B that functions as the electrode 3B is arranged at the first position. At this time, as shown in FIG. 43, since the proximal-end portion 31 of the water-supply pipeline 2B and the distal-end end portion of the electrode 415 are separated from each other, it is possible to prevent the high frequency current from being applied to the treatment region R which is contrary to the intention of the surgeon.

As described above, it is possible to advance and retract the water-supply pipeline 2B in response to the advancement and retraction of the slider 43B with respect to the operation portion main body 40, and it is possible to switch the energized state and the non-energized state of the high frequency current to the water-supply pipeline 2B that functions as the electrode 3B.

Although the respective embodiments and modifications of the present disclosure have been described above, the technical scope of the present disclosure is not limited to the above-described embodiments, and configurations in the respective embodiments and modifications within the scope not departing from the spirit of the present disclosure. It is possible to change the combination of elements, make various changes to each configuration element, or delete each configuration element. For example, the configuration according to any one of above-described embodiments and modifications of the present disclosure may be appropriately combined with each modification of the operation portion. The present disclosure is not limited by the above description, but only by the appended claims.

What is claimed is:

1. A treatment device, comprising:
   a pipeline configured to deliver liquid therethrough;
   a wire that is inserted through the pipeline, the wire being advanceable and retractable with respect to the pipeline, the wire being a first conductor;
   a handle main body located at a proximal end of the pipeline;
   a slider attached to the handle main body; and
   a second conductor fixed with respect to the handle main body, wherein
   a proximal-end portion of the wire and the second conductor are configured to electrically switch between a contact state and a non-contact state in response to movement of the slider with respect to the handle main body.

2. The treatment device according to claim 1, further comprising a distal-end tip attached to a distal end of the pipeline, the distal-end tip including a distal-end opening that is in communication with an internal space of the pipeline.

3. The treatment device according to claim 2, wherein the distal-end tip includes side openings that are formed in a lateral side of the distal-end tip, and are in communication with the internal space of the pipeline.

4. The treatment device according to claim 3, wherein the side openings are slits that are also in communication with the distal-end opening.

5. The treatment device according to claim 1, wherein the distal end of the wire is configured to puncture tissue.

6. The treatment device according to claim 1, wherein the pipeline is configured to be moved along an axial direction of the pipeline with respect to the wire between: (i) a first position in which a distal end of the pipeline is located distally relative to a distal end of the wire in the axial direction, and (ii) a second position at which the distal end of the pipeline is located proximally relative to the distal end of the wire in the axial direction.

7. The treatment device according to claim 1, wherein the slider is connected to the wire in the handle main body.

8. A treatment device, comprising:
   a gas pipeline;
   a liquid pipeline;
   a wire that is inserted through the liquid pipeline, the wire being advanceable and retractable with respect to the liquid pipeline;
   a handle main body that is attached to a proximal end of the gas pipeline;
   a slider attached to the handle main body, the slider being connected to the wire in the handle main body; and
   a conductor that is fixed with respect to the handle main body, wherein
   a proximal-end portion of the wire and the conductor are configured to electrically switch between a contact state and a non-contact state in response to a movement of the slider with respect to the handle main body.

9. The treatment device according to claim 8, further comprising a distal-end tip attached to a distal end of the gas pipeline, the distal-end tip including a distal-end opening that is in communication with an internal space of the gas pipeline.

10. The treatment device according to claim 9, wherein the distal-end tip includes side openings that are formed in a lateral side of the distal-end tip, and are in communication with the internal space of the gas pipeline.

11. The treatment device according to claim 10, wherein the side openings are slits that are in communication with the distal-end opening.

12. The treatment device according to claim 8, wherein the distal end of the wire is configured to puncture tissue.

13. The treatment device according to claim 8, wherein the liquid pipeline is configured to be moved along an axial direction of the gas pipeline with respect to the gas pipeline between: (i) a first position in which a distal end of the liquid pipeline is located distally relative to a distal-end opening of the gas pipeline in the axial direction of the gas pipeline, and (ii) a second position at which the distal end of the liquid pipeline is located proximally relative to the distal-end opening in the axial direction.

14. The treatment device according to claim 8, wherein the wire is a conductor.

* * * * *